United States Patent
Augustine et al.

(10) Patent No.: US 10,206,248 B2
(45) Date of Patent: Feb. 12, 2019

(54) HEATED UNDERBODY WARMING SYSTEMS WITH ELECTROSURGICAL GROUNDING

(71) Applicant: Augustine Temperature Management LLC, Eden Prairie, MN (US)

(72) Inventors: Scott D. Augustine, Deephaven, MN (US); Randall C. Arnold, Minnetonka, MN (US); Scott A. Entenman, St. Paul, MN (US); Rudolf A. Deibel, Eden Prairie, MN (US); Garrett J. Augustine, Deephaven, MN (US)

(73) Assignee: Augustine Temperature Management LLC, Eden Prairie, MN (US)

( * ) Notice: Subject to any disclaimer, the term of this patent is extended or adjusted under 35 U.S.C. 154(b) by 344 days.

(21) Appl. No.: 14/940,828

(22) Filed: Nov. 13, 2015

(65) Prior Publication Data
US 2016/0143091 A1    May 19, 2016

Related U.S. Application Data

(60) Provisional application No. 62/079,076, filed on Nov. 13, 2014.

(51) Int. Cl.
*H05B 1/02* (2006.01)
*H05B 3/36* (2006.01)
(Continued)

(52) U.S. Cl.
CPC ............ *H05B 3/36* (2013.01); *A47C 21/048* (2013.01); *A61B 18/16* (2013.01); *A61F 7/007* (2013.01);
(Continued)

(58) Field of Classification Search
CPC .......... H05B 3/36; H05B 3/146; H05B 3/142; H05B 2203/011; H05B 2203/013;
(Continued)

(56) References Cited

U.S. PATENT DOCUMENTS 2,403,676 A   7/1946 Modlinski
2,497,186 A   2/1950 Pedersen
(Continued)

FOREIGN PATENT DOCUMENTS

DE   3343664 C1   3/1985
DE   10065592 A1  7/2002
(Continued)

OTHER PUBLICATIONS

International Search Report and the Written Opinion of the International Searching Authority, or the Declaration for International Pat. App. No. PCT/US2015/025392, dated Jul. 16, 2015, 13 pages, European Patent Office, Rijswijk, The Netherlands.
(Continued)

*Primary Examiner* — Mark Paschall
(74) *Attorney, Agent, or Firm* — Fredrikson & Byron, P.A.

(57) ABSTRACT

Embodiments include a heated underbody support with electrosurgical grounding, such as a heated mattress, heated mattress overlay, or heated pad for supporting a person. The heated underbody support may include a flexible heating element formed of a sheet of conductive or semi-conductive material, a first bus bar along a first edge of the heating element adapted to receive a supply of electrical power, a second bus bar extending along the second edge of the heating element, and a temperature sensor. The heated underbody support may include a layer of compressible material adapted to conform to the person under pressure from the person resting upon the support located beneath the
(Continued)

heating element. A water resistant shell may encase the heating element, the first and second bus bars, and the temperature sensor. A return electrode wire may be electrically connected to the flexible heating element to connect to an electrosurgical generator.

26 Claims, 21 Drawing Sheets

(51) Int. Cl.
    *A47C 21/04*     (2006.01)
    *A61F 7/00*     (2006.01)
    *A61B 18/16*     (2006.01)
    *H05B 3/34*     (2006.01)
    *H05B 3/14*     (2006.01)

(52) U.S. Cl.
    CPC ........... *A61F 7/0097* (2013.01); *H05B 3/146* (2013.01); *H05B 3/342* (2013.01); *A61B 2018/167* (2013.01); *A61F 2007/0071* (2013.01); *H05B 2203/011* (2013.01); *H05B 2203/013* (2013.01); *H05B 2203/016* (2013.01)

(58) Field of Classification Search
    CPC ........... H05B 2203/016; A47C 21/048; A61B 2018/167; A61B 18/16; A61F 7/0097; A61F 2007/0071
    USPC ....... 219/528, 529, 541, 544, 545, 549, 505, 219/494, 211, 212, 497
    See application file for complete search history.

(56) References Cited

U.S. PATENT DOCUMENTS

| | | |
|---|---|---|
| 2,706,768 A | 4/1955 | Kaplan |
| 2,715,674 A | 8/1955 | Abbott |
| 3,008,152 A | 11/1961 | Seidenberg |
| 3,134,891 A | 5/1964 | Hyer |
| 3,137,871 A | 6/1964 | Florio |
| 3,340,549 A | 9/1967 | Billerbeck |
| 3,380,087 A | 4/1968 | Petty et al. |
| 3,582,456 A | 6/1971 | Stolki |
| 3,634,655 A | 1/1972 | Jordan |
| 3,690,325 A | 9/1972 | Kenny |
| 3,780,262 A | 12/1973 | Rudd |
| 3,808,403 A | 4/1974 | Gunma |
| 3,839,621 A | 10/1974 | Hariu |
| 3,854,156 A | 12/1974 | Williams |
| 3,874,504 A | 4/1975 | Verakas |
| 3,900,654 A | 8/1975 | Stinger |
| 3,936,661 A | 2/1976 | Furuishi |
| 4,061,898 A | 12/1977 | Murray |
| 4,118,531 A | 10/1978 | Hauser |
| 4,149,066 A | 4/1979 | Niibe |
| 4,186,294 A | 1/1980 | Bender |
| 4,250,398 A | 2/1981 | De Fonso et al. |
| 4,270,040 A | 5/1981 | McMullan et al. |
| 4,363,947 A | 12/1982 | Bergersen et al. |
| 4,423,308 A | 12/1983 | Callaway |
| 4,479,795 A | 10/1984 | Mustacich |
| 4,495,402 A | 1/1985 | Burdick |
| 4,534,886 A | 8/1985 | Kraus |
| 4,626,664 A | 12/1986 | Grise |
| 4,658,119 A | 4/1987 | Endo et al. |
| 4,660,388 A | 4/1987 | Greene, Jr. |
| 4,661,689 A | 4/1987 | Harrison |
| 4,676,247 A | 6/1987 | Van Cleve |
| 4,682,447 A | 7/1987 | Osborn |
| 4,691,762 A | 9/1987 | Elkins et al. |
| 4,719,335 A | 1/1988 | Batliwalla |
| 4,747,409 A | 5/1988 | Silen |
| 4,764,665 A | 8/1988 | Orban |
| 4,798,936 A | 1/1989 | Johnson |
| 4,899,749 A | 2/1990 | Laroco |
| 4,912,306 A | 3/1990 | Grise |
| 4,930,317 A | 6/1990 | Klein |
| 4,941,961 A | 7/1990 | Noguchi et al. |
| 4,989,283 A | 2/1991 | Krouskop et al. |
| 5,008,515 A | 4/1991 | McCormack |
| 5,010,233 A | 4/1991 | Henschen |
| 5,023,433 A | 6/1991 | Gordon |
| 5,032,705 A | 7/1991 | Batcheller et al. |
| 5,072,598 A | 12/1991 | Dibrell et al. |
| 5,074,285 A | 12/1991 | Wright |
| 5,086,629 A | 2/1992 | Dibrell et al. |
| 5,255,390 A | 10/1993 | Gross et al. |
| 5,320,164 A | 6/1994 | Szczesuil et al. |
| 5,352,870 A | 10/1994 | Daugherty et al. |
| 5,380,580 A | 1/1995 | Rogers |
| 5,383,918 A | 1/1995 | Panetta et al. |
| 5,395,399 A | 3/1995 | Rosenwald |
| 5,422,462 A | 6/1995 | Kishimoto |
| 5,443,056 A | 8/1995 | Smith |
| 5,473,783 A | 12/1995 | Allen |
| 5,496,358 A | 3/1996 | Rosenwald et al. |
| 5,534,021 A | 7/1996 | Dvoretzky et al. |
| 5,605,144 A | 2/1997 | Simmons et al. |
| 5,638,438 A | 6/1997 | Keen et al. |
| 5,723,845 A | 3/1998 | Partington |
| 5,755,275 A | 5/1998 | Rose et al. |
| 5,773,275 A | 6/1998 | Anderson |
| 5,815,864 A | 10/1998 | Sloop |
| 5,817,145 A | 10/1998 | Augustine |
| 5,824,996 A | 10/1998 | Kochman |
| 5,835,983 A | 11/1998 | McMahen et al. |
| 5,878,620 A | 3/1999 | Gilbert et al. |
| 5,881,410 A | 3/1999 | Yamada |
| 5,895,973 A | 4/1999 | Fessenden |
| 5,928,274 A | 7/1999 | Augustine |
| 5,932,129 A | 8/1999 | Hyatt |
| 5,948,303 A | 9/1999 | Larson |
| 5,964,792 A | 10/1999 | Augustine |
| 5,970,542 A | 10/1999 | Mays |
| 5,974,605 A | 11/1999 | Dickerhoff |
| 5,986,243 A | 11/1999 | Campf |
| 6,030,412 A | 2/2000 | Klatz et al. |
| 6,038,722 A | 3/2000 | Giori et al. |
| 6,053,910 A | 4/2000 | Fleenor |
| 6,078,026 A | 6/2000 | West |
| 6,084,217 A | 7/2000 | Bulgajewski |
| 6,093,910 A | 7/2000 | McClintock |
| 6,147,333 A | 11/2000 | Mattson |
| 6,149,674 A | 11/2000 | Borders |
| 6,172,344 B1 | 1/2001 | Gordon |
| 6,180,929 B1 | 1/2001 | Pearce |
| 6,184,496 B1 * | 2/2001 | Pearce .................. E01C 11/265 |
| | | 219/202 |
| 6,189,487 B1 | 2/2001 | Owen |
| 6,210,427 B1 | 4/2001 | Augustine |
| 6,214,000 B1 | 4/2001 | Fleenor |
| 6,215,111 B1 | 4/2001 | Rock |
| 6,229,123 B1 | 5/2001 | Kochman |
| 6,229,126 B1 | 5/2001 | Ulrich et al. |
| 6,235,049 B1 | 5/2001 | Nazerian |
| 6,240,623 B1 | 6/2001 | Johansson |
| 6,348,678 B1 | 2/2002 | Loyd, Sr. et al. |
| 6,373,034 B1 | 4/2002 | Rock |
| 6,403,935 B2 | 6/2002 | Kochman |
| 6,416,534 B1 | 7/2002 | Montagnino et al. |
| 6,434,328 B2 | 8/2002 | Rutherford |
| 6,452,138 B1 | 9/2002 | Kochman |
| 6,452,139 B1 | 9/2002 | Benoit et al. |
| 6,483,087 B2 | 11/2002 | Gardner |
| 6,493,889 B2 | 12/2002 | Kocurek |
| 6,544,258 B2 * | 4/2003 | Fleenor .................. A61B 18/16 |
| | | 128/908 |
| 6,565,593 B2 | 5/2003 | Diana |
| 6,582,456 B1 | 6/2003 | Hand |
| 6,705,388 B1 | 3/2004 | Sorgo |
| 6,713,733 B2 | 3/2004 | Kochman et al. |
| 6,723,115 B1 | 4/2004 | Daly |

(56) References Cited

U.S. PATENT DOCUMENTS

| | | | |
|---|---|---|---|
| 6,730,115 B1 | 5/2004 | Heaton | |
| 6,755,852 B2 | 6/2004 | Lachenbruch et al. | |
| 6,770,848 B2 | 8/2004 | Haas | |
| 6,770,854 B1 | 8/2004 | Keane | |
| 6,839,922 B1 | 1/2005 | Foggett | |
| 6,872,758 B2 | 3/2005 | Simpson | |
| 6,924,467 B2 | 8/2005 | Ellis | |
| 6,933,469 B2 | 8/2005 | Ellis | |
| 6,967,309 B2* | 11/2005 | Wyatt | A61F 7/00 219/217 |
| 6,974,935 B2 | 12/2005 | O'Grady | |
| 7,013,509 B2 | 3/2006 | Hickman | |
| 7,020,912 B2 | 4/2006 | Berge | |
| 7,022,950 B2 | 4/2006 | Haas | |
| 7,049,559 B2 | 5/2006 | Ishii et al. | |
| 7,053,344 B1 | 5/2006 | Surjan | |
| 7,107,629 B2 | 9/2006 | Miros et al. | |
| 7,161,120 B1 | 1/2007 | Stroud | |
| 7,176,419 B2 | 2/2007 | Ellis | |
| 7,181,790 B2 | 2/2007 | Wirtz et al. | |
| 7,228,578 B2 | 6/2007 | Linnane | |
| 7,268,320 B2 | 9/2007 | Rock et al. | |
| 7,282,676 B1 | 10/2007 | Bouchier et al. | |
| 7,375,308 B2 | 5/2008 | Ferguson | |
| 7,543,344 B2 | 6/2009 | Augustine | |
| 7,714,255 B2 | 5/2010 | Augustine | |
| 7,851,729 B2 | 12/2010 | Augustine | |
| 8,062,343 B2 | 11/2011 | Augustine et al. | |
| 8,065,763 B2 | 11/2011 | Brykalski | |
| 8,170,685 B2 | 5/2012 | Docherty et al. | |
| 8,283,602 B2 | 10/2012 | Augustine | |
| 8,288,693 B2 | 10/2012 | Weiss | |
| 8,291,612 B2 | 10/2012 | Ferguson | |
| 8,418,297 B2 | 4/2013 | Mikkelsen | |
| 8,624,164 B2 | 1/2014 | Deibel | |
| 8,698,044 B2 | 4/2014 | Burr | |
| 8,772,676 B2 | 7/2014 | Augustine | |
| 8,876,812 B2* | 11/2014 | Aramayo | A61B 18/16 606/32 |
| 2001/0020303 A1 | 9/2001 | Endo | |
| 2002/0005398 A1 | 1/2002 | Gillner | |
| 2002/0047007 A1 | 4/2002 | Loyd, Sr. et al. | |
| 2002/0073489 A1 | 6/2002 | Totton et al. | |
| 2002/0117495 A1 | 8/2002 | Kochman | |
| 2002/0124312 A1 | 9/2002 | Yoon | |
| 2003/0023292 A1 | 1/2003 | Gammons et al. | |
| 2003/0069621 A1 | 4/2003 | Kushnir | |
| 2003/0192121 A1 | 10/2003 | Fleming et al. | |
| 2003/0195596 A1 | 10/2003 | Augustine et al. | |
| 2003/0208848 A1 | 11/2003 | Flick et al. | |
| 2004/0149711 A1 | 8/2004 | Wyatt | |
| 2004/0164499 A1 | 8/2004 | Murakami | |
| 2004/0174056 A1 | 9/2004 | Gryp et al. | |
| 2004/0193237 A1 | 9/2004 | Krueger | |
| 2004/0237206 A1 | 12/2004 | Webster | |
| 2005/0016982 A1 | 1/2005 | Campf | |
| 2005/0051537 A1 | 3/2005 | Lewis | |
| 2005/0061122 A1 | 3/2005 | Behringer | |
| 2005/0061681 A1 | 3/2005 | Lim et al. | |
| 2005/0103353 A1 | 5/2005 | Grahn et al. | |
| 2006/0085919 A1 | 4/2006 | Kramer et al. | |
| 2006/0120054 A1 | 6/2006 | Buschke | |
| 2006/0142828 A1 | 6/2006 | Schorr et al. | |
| 2006/0191675 A1 | 8/2006 | Fletcher et al. | |
| 2006/0247745 A1 | 11/2006 | Thompson | |
| 2006/0260060 A1 | 11/2006 | Apperson | |
| 2006/0261055 A1 | 11/2006 | Child et al. | |
| 2007/0012675 A1 | 1/2007 | Devroy | |
| 2007/0049997 A1 | 3/2007 | Fields et al. | |
| 2007/0068916 A1 | 3/2007 | Augustine et al. | |
| 2007/0068923 A1* | 3/2007 | Augustine | A61F 7/007 219/465.1 |
| 2007/0068928 A1 | 3/2007 | Augustine et al. | |
| 2007/0068929 A1 | 3/2007 | Augustine et al. | |
| 2007/0068930 A1 | 3/2007 | Augustine | |
| 2007/0068931 A1 | 3/2007 | Augustine et al. | |
| 2007/0068932 A1 | 3/2007 | Augustine et al. | |
| 2007/0080155 A1 | 4/2007 | Augustine et al. | |
| 2007/0093883 A1 | 4/2007 | Anderson et al. | |
| 2007/0101996 A1 | 5/2007 | Carstens | |
| 2007/0106353 A1 | 5/2007 | Carstens | |
| 2007/0106355 A1 | 5/2007 | Carstens | |
| 2007/0108190 A1 | 5/2007 | Ferguson | |
| 2007/0152479 A1 | 7/2007 | Howman | |
| 2007/0164010 A1 | 7/2007 | Rock | |
| 2007/0272673 A1 | 11/2007 | Keane | |
| 2007/0284356 A1 | 12/2007 | Findlay | |
| 2008/0021530 A1 | 1/2008 | Castellani et al. | |
| 2008/0127414 A1 | 6/2008 | Allen | |
| 2008/0173629 A1* | 7/2008 | Deibel | A61F 7/007 219/212 |
| 2008/0203080 A1 | 8/2008 | Fung | |
| 2008/0217587 A1 | 9/2008 | Gaudiana et al. | |
| 2008/0249521 A1 | 10/2008 | Dunning et al. | |
| 2008/0249524 A1 | 10/2008 | Dunning | |
| 2008/0255641 A1 | 10/2008 | Ellis | |
| 2008/0281310 A1 | 11/2008 | Dunning et al. | |
| 2008/0281311 A1 | 11/2008 | Dunning et al. | |
| 2008/0283513 A1 | 11/2008 | Ferguson | |
| 2009/0036884 A1 | 2/2009 | Gregg et al. | |
| 2009/0078690 A1 | 3/2009 | Lee | |
| 2009/0095735 A1 | 4/2009 | Resheff | |
| 2009/0099630 A1* | 4/2009 | Augustine | A61F 7/0097 607/96 |
| 2009/0099631 A1* | 4/2009 | Augustine | A61F 7/007 607/104 |
| 2009/0163984 A1 | 6/2009 | Robinson et al. | |
| 2009/0198230 A1 | 8/2009 | Behnke et al. | |
| 2009/0222996 A1 | 9/2009 | Balonick | |
| 2010/0078807 A1 | 4/2010 | Schulz | |
| 2010/0089896 A1 | 4/2010 | Bart | |
| 2010/0119704 A1 | 5/2010 | Hemmelgarn | |
| 2010/0161016 A1 | 6/2010 | Augustine | |
| 2010/0168825 A1 | 7/2010 | Barbknecht | |
| 2010/0200558 A1 | 8/2010 | Liu et al. | |
| 2010/0204763 A1 | 8/2010 | Augustine | |
| 2010/0222457 A1 | 9/2010 | Wanner | |
| 2010/0224612 A1 | 9/2010 | Asami | |
| 2010/0279086 A1 | 11/2010 | Park et al. | |
| 2010/0283295 A1 | 11/2010 | Smith | |
| 2010/0325796 A1 | 12/2010 | Lachenbruch | |
| 2011/0031230 A1 | 2/2011 | Kim | |
| 2011/0092930 A1 | 4/2011 | Poorman | |
| 2011/0099900 A1 | 5/2011 | Weder | |
| 2011/0233185 A1 | 9/2011 | Augustine et al. | |
| 2012/0065716 A1 | 3/2012 | Gill et al. | |
| 2012/0111846 A1 | 5/2012 | Hammerschmidt | |
| 2012/0140375 A1 | 6/2012 | Kim et al. | |
| 2012/0222192 A1 | 9/2012 | Carey et al. | |
| 2012/0238842 A1 | 9/2012 | Colvin, Jr. et al. | |
| 2012/0238901 A1 | 9/2012 | Augustine | |
| 2012/0273475 A1 | 11/2012 | An | |
| 2012/0279953 A1* | 11/2012 | Augustine | A61G 13/12 219/217 |
| 2014/0074086 A1 | 3/2014 | MacIntyre-Ellis | |
| 2014/0263265 A1 | 9/2014 | Augustine et al. | |
| 2014/0312027 A1 | 10/2014 | Augustine | |
| 2014/0316494 A1 | 10/2014 | Augustine | |
| 2014/0316495 A1 | 10/2014 | Augustine | |
| 2015/0148874 A1 | 5/2015 | Augustine et al. | |
| 2015/0216610 A1 | 8/2015 | Augustine | |
| 2015/0289817 A1 | 10/2015 | Augustine et al. | |
| 2015/0290027 A1 | 10/2015 | Augustine et al. | |
| 2015/0290062 A1 | 10/2015 | Augustine et al. | |
| 2015/0290065 A1 | 10/2015 | Augustine | |
| 2015/0327332 A1 | 11/2015 | Augustine et al. | |
| 2015/0366367 A1 | 12/2015 | Augustine et al. | |
| 2015/0373781 A1 | 12/2015 | Augustine et al. | |

FOREIGN PATENT DOCUMENTS

| | | |
|---|---|---|
| EP | 787476 A2 | 8/1997 |
| EP | 1374822 A1 | 1/2004 |

(56) References Cited

FOREIGN PATENT DOCUMENTS

| EP | 2662063 A1 | 11/2013 |
|---|---|---|
| GB | 586745 A | 3/1947 |
| GB | 969253 A | 9/1964 |
| WO | 9925155 A1 | 5/1999 |
| WO | 1999023992 A1 | 5/1999 |
| WO | 0135878 A2 | 5/2001 |
| WO | 2001095841 A1 | 7/2002 |
| WO | 2004093758 A1 | 11/2004 |
| WO | 2007041389 A1 | 4/2007 |
| WO | 2008089412 A1 | 7/2008 |
| WO | 2010107724 A1 | 9/2010 |
| WO | 2012125916 A2 | 9/2012 |
| WO | 2013134477 A1 | 9/2013 |
| WO | 2015157674 A2 | 10/2015 |
| WO | 2015157684 A1 | 10/2015 |

OTHER PUBLICATIONS

International Search Report and the Written Opinion of the International Searching Authority, or the Declaration for International Pat. App. No. PCT/US2015/060659, dated Feb. 5, 2016, 12 pages, European Patent Office, Rijswijk, The Netherlands.

Bair Hugger brochure, retrieved from http://www.bairhugger.com/arizanthealthcare/pdf/600755A.pdf, 2003, 6 pages.

Lenhardt et al., "Local warming and insertion of peripheral venous cannulas: single blinded prospective randomised controlled trial and single blinded randomised crossover trial," British Medical Journal 325:409, Aug. 2002, 4 pages.

Moritz and Henriques, "Studies of Thermal Injury: The Relative Importance of Time and Surface Temperature in the Causation of Cutaneous Burns", Am. J. Pathology 23:, Am. J. Pathology 23:695-720, 1947; retrieved Feb. 15, 2016 from the Internet <URL: http://www.ncbi.nlm.nih.gov/pmc/articles/PMC1934331/pdf/amjpathol00503-0003.pdf>.

Stoll & Greene, "Relationship Between Pain and Tissue Damage Due to Thermal Radiation", J. Applied Physiol, J. Applied Physiology 14 (3):373-382, 1959.

EeonTex Conductive Textiles, Product Details, www.eeonyx.com/prodte.html, Sep. 19, 2006, 4 pages, retrieved =Feb. 15, 2016 from the Internet <URL: http://web.archive.org/web/20061010102213/http://eeonyx.com/prodte.html.

Supplementary European Search Report for EP Pat. App. No. 12757173, dated May 22, 2015, 9 pages, European Patent Office, Munich, Germany.

International Search Report and the Written Opionion of the International Searching Authority, or the Declaration for International Pat. App. No. PCT/US2015/025392, dated Jul. 16, 2015, 13 pages, European Patent Office, Rijswijk, The Netherlands.

Invitation to Pay Additional Fees and, Where Applicable, Protest Fee for International Pat. App. No. PCT/US2015/025374, dated Jul. 20, 2015, 6 pages, European Patent Office, Rijswijk, The Netherlands.

International Search Report and the Written Opionion of the International Searching Authority, or the Declaration for International Pat. App. No. PCT/US2015/025374, dated Nov. 9, 2015, 15 pages, European Patent Office, Rijswijk, The Netherlands.

* cited by examiner

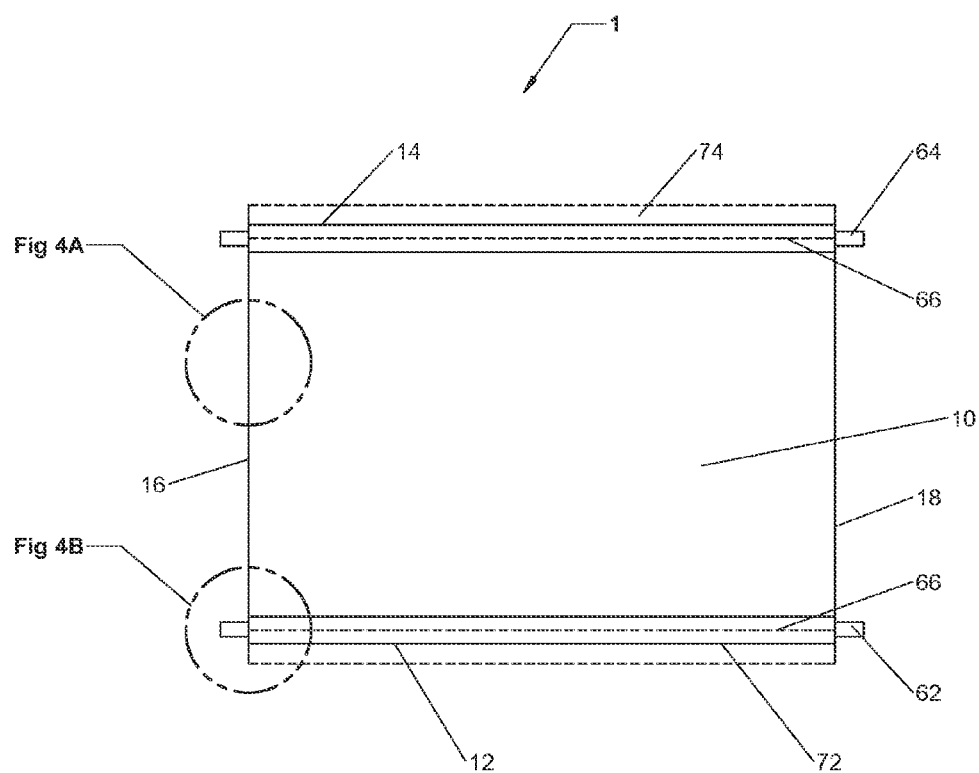

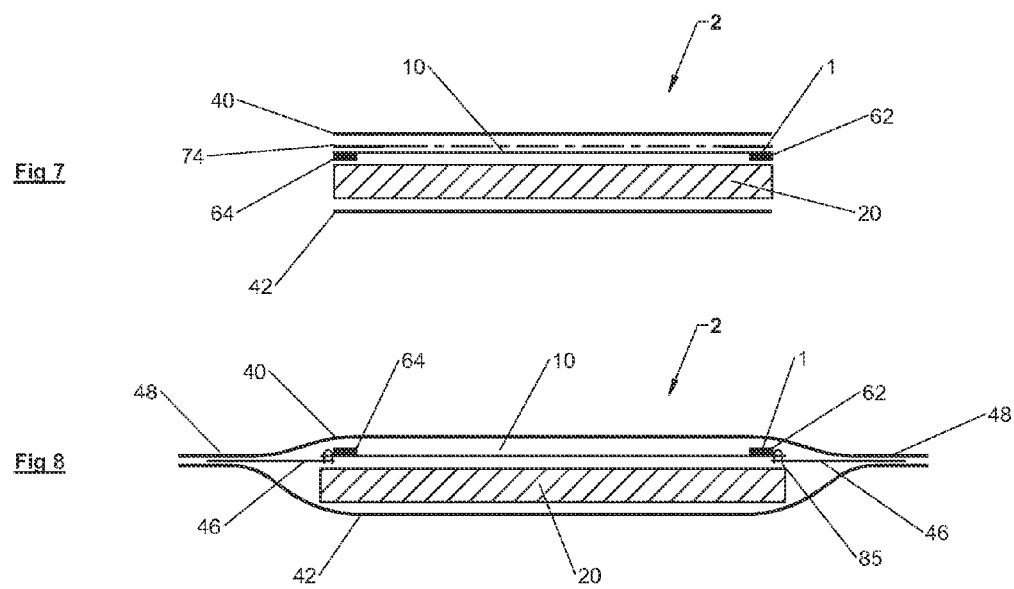

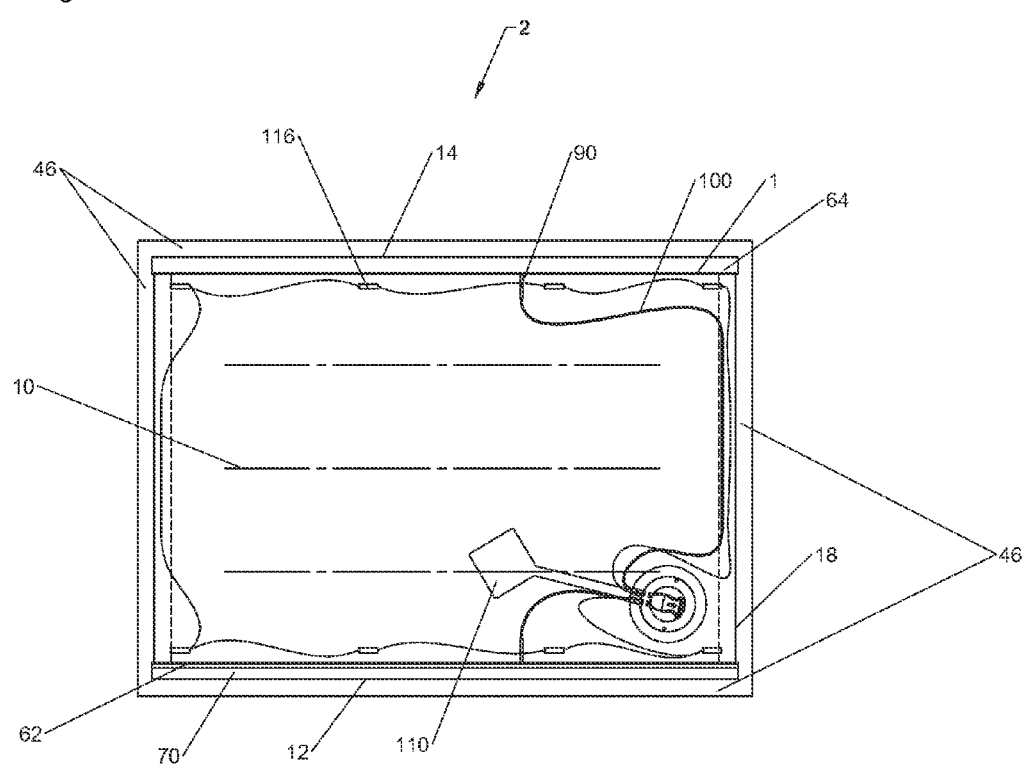

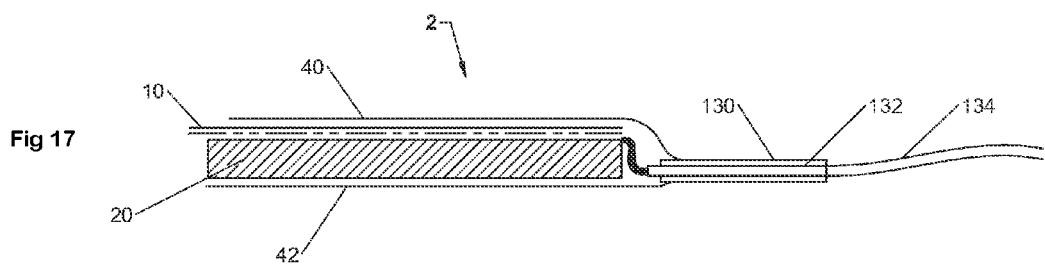

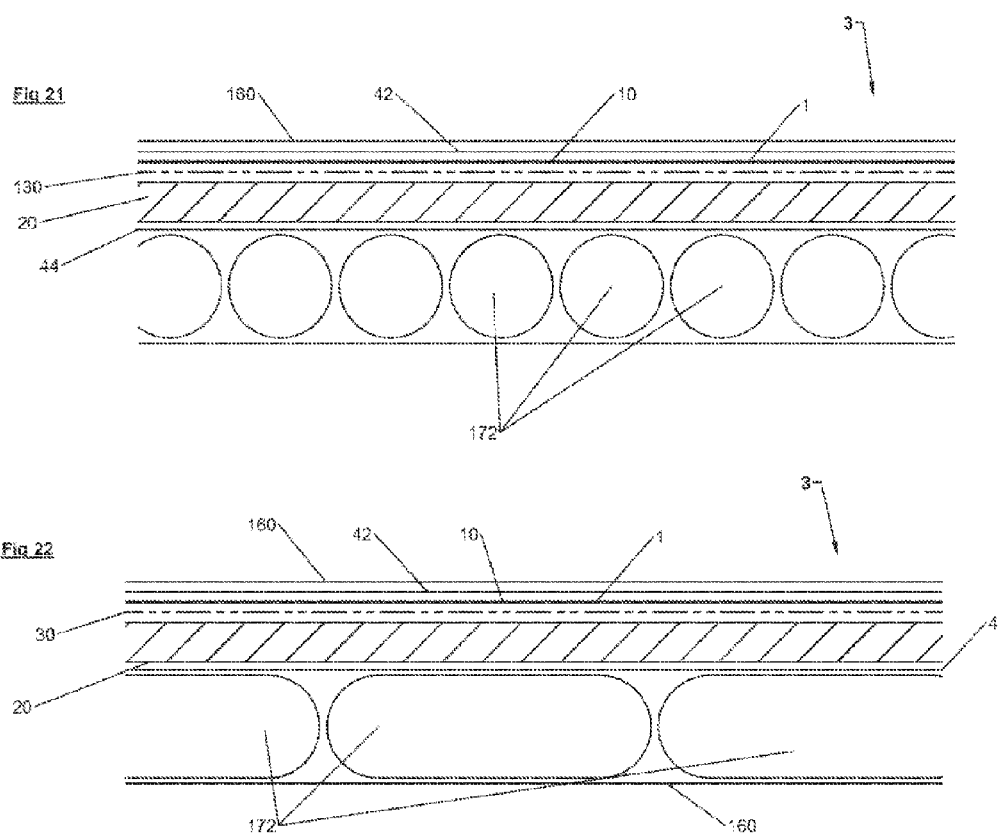

HEATED UNDERBODY WARMING SYSTEMS WITH ELECTROSURGICAL GROUNDING

PRIORITY CLAIM

The present application claims priority to U.S. Provisional Patent Application 62/079,076, filed Nov. 13, 2014, the entire contents of which are incorporated herein by reference.

RELATED APPLICATIONS

The present application is related to U.S. patent application Ser. No. 14/842,496 filed Sep. 1, 2015, which claimed priority to U.S. 62/079,076 filed Nov. 13, 2014. The present application is related to U.S. patent application Ser. No. 14/683,825, filed Apr. 10, 2015, and PCT Application US 2015/025374 filed Apr. 10, 2015, of which both claimed priority to U.S. Provisional Patent Application 61/977,930, filed Apr. 10, 2014. The present application is also related to U.S. patent application Ser. No. 13/422,279, filed Mar. 16, 2012, which claimed priority to U.S. Provisional Application No. 61/453,311, filed Mar. 16, 2011. In addition, the present application is related to U.S. Provisional Patent Application 61/812,987, filed Apr. 17, 2013. All of the related applications are incorporated herein by reference.

BACKGROUND

There have been many attempts at making heated mattresses and heated mattress overlays for therapeutic patient warming. Therapeutic patient warming is especially important for patients during surgery. It is well known that without therapeutic intra-operative warming, most anesthetized surgical patients will become clinically hypothermic during surgery. Hypothermia has been linked to increased wound infections, increased blood loss, increased cardiac morbidity, prolonged ICU time, prolonged hospital stays, increased cost of surgery and increased death rates.

Since the early 1990s, the standard of care for surgical warming has been forced air warming blankets. Prior to that time, warm water mattresses were commonly used. The warm water mattresses went out of common use because they were relatively stiff and inflexible. The stiff water mattress negated any pressure relief that the underlaying support mattress may have provided. As a result, the combination of pressure applied to the boney prominences and the heat from the warm water mattress both reduced blood flow and accelerated metabolism, causing accelerated ischemic pressure injuries to the skin ("bed sores"). Additionally, the warmed water recirculating in the warming system was well known to be grossly contaminated with bacteria, which was especially important when a leak occurred. As a result, warm water mattresses are rarely used today.

Historically, electrically heated pads and blankets for the consumer market have been made with resistive wire heaters. Wire-based heaters have been questionably safe in consumer use. However, in the operating room environment with anesthetized patients, hot spots caused by the wires in normal use and the failure mode of broken heater wires resulting in sparking, arcing and fires are totally unacceptable. Therefore, resistive wire-based heaters are not used in the operating room today.

Since the mid 1990's, a number of inventors have tried unsuccessfully to make effective and safe heated mattresses for operating room use, using flexible, sheet-like electric resistance heaters. The sheet-like heaters have been shown to be more effective in warming the patients because of the even heat production and generally do not cause arcing and sparking when they fail.

Some existing devices employ sheet-like heaters using a polymeric fabric that has been baked at high temperature until it becomes carbonized and is thus conductive of electricity. The carbonization process makes the fabric fragile, and therefore, it may be laminated between two layers of plastic film or fiber-reinforced plastic film for stability and strength. The lamination process results in a relatively stiff, although somewhat flexible, non-stretching, non-conforming heater. The metal foil bus bars are attached to the heater material with an "electrically conductive adhesive or bonding composition . . . " and then encapsulated with polyurethane-coated nylon fabric. The result is a stiff and relatively inflexible bus bar.

Other sheet-like heaters found in some existing devices use a carbon-filled electrically conductive ink, printed on and laminated between two sheets of polyester film. The copper braid bus bars are "suspended" in the carbon-filled plastic and also laminated between the two sheets of polyester film. The resulting heater and bus bar assembly is relatively stiff, non-conforming and totally non-stretching. Because the heater is relatively stiff, a layer of foam, preferably greater than 1.5 inches thick (0.25-3 inches), can be placed between the heater and the patient. This thick layer of foam may pad the patient from the stiff heater, but it also introduces a thermal insulation between the heater and the patient, making the mattress ineffective for patient warming. Finally, the heater elements of this invention are similar to flat wires and are not "sheet-like." Polyester film can be cut out of the large spaces between the individual heater elements in order to improve flexibility. With this design, it is impossible to produce even heat across the surface of the pad, as it would be with any wire heater for use in a warming pad. It is hot where the wire is located and cold in between the wires.

In other devices, the heater material is a carbon impregnated plastic film. The film contains >50% carbon by weight. The carbon-laden plastic film is relatively weak and non-elastic and therefore is extruded or laminated onto a woven fabric for stability and to prevent tearing. The metal film and woven wire bus bars are bonded to the conductive plastic with a conductive adhesive and then potted in a thick layer of plastic for durability and strength. The fabric-reinforced film heater is relatively flexible, but is not stretchable or elastic. The potted bus bars are relatively inflexible and totally non-stretchable. Such devices can include a thick layer of high-loft fibrous thermal insulation placed between the heater and the upper surface of the mattress/patient. This thermal insulation reduces the effectiveness of the mattress for patient warming.

Electrically conductive fabric made of carbon fibers has been used as heater material in therapeutic blankets. However, carbon fiber fabric has not been used for therapeutic mattresses. Carbon fiber fabric may be stabilized by laminating it between layers of plastic film in order to keep the "slippery" fiber bundles from shifting randomly and altering the conductivity and heat production. Additionally, the carbon fibers are known to fracture over time with repeated flexing, which also changes the conductivity. Fiber fracturing can be minimized by laminating the fabric between layers of plastic film. The stiffer the resultant laminate, the more protective of the fibers. However, stiff heaters are not optimal when used in therapeutic heating blankets and mattresses because they are opposite of localized pressure reduction. Finally, carbon fiber fabric is known to not heat evenly, often resulting in "hot spots." Skin is fairly intolerant of heat and therefore the temperature of the applied heat from the mattress is preferably accurately and tightly controlled. If the temperature of the heater is not even, accurate control is impossible.

In summary, designs that incorporate electrically conductive fabric heaters are of necessity relatively stiff because of the need to be laminated between two layers of plastic film. These laminated heaters are somewhat flexible and can be deformed into a simple curve. However, they do not respond to point pressure applied to their surfaces and deform into three-dimensional compound curves resembling a half sphere without folding and wrinkling. This is because these laminates do not stretch. Stretching would desirably provide evenly distributed, non-wrinkling 3-dimensional deformation. Finally, these heaters all utilize bonding and laminating or potting of the bus bars to the heater material in order to assure a durable electrical connection attempting to avoid "hot" bus bar failures. The heaters become very inflexible and totally non-stretchable in the areas of the bus bars. Therefore, these laminated fabric heaters have limited utility for use in pressure-reducing therapeutic mattresses.

Conductive and semi-conductive films are often made into heaters by applying the film to a relatively non-stretchable fabric because the carbon-laden plastic film is relatively weak and inelastic and because even if the film did not tear while stretching, it would not return to its original planar shape when the deforming pressure is removed.

Another existing device includes an inflatable air mattress with a single air chamber and a heater incorporating a resistive wire heating element stretched across its upper surface. This mattress design may be suitable for home use, but the single chamber design is not maximally accommodating and is relatively unstable for surgical table use. The wire heating element is totally unsuitable for use in the operating room. Finally, the heater is attached to the mattress around its edges and, thus, would exhibit hammocking when deformed by the weight of a patient.

Maximal patient warming effectiveness is achieved by maximally accommodating the patient into the mattress. In other words, maximizing the contact area between the patient's skin and the heated surface of the mattress. The heater and the foam or air bladders of the mattress may be easily deformable to allow the patient to sink into the mattress. This accommodation maximizes the patients skin surface area in contact with the mattress and heater, which minimizes the pressure applied to any given point. It also maximizes the surface contact area for heat transfer and maximizes blood flow to the skin in contact with the heat for optimal heat transfer. The accommodation of the patient into the mattress may not be hindered by a stiff, non-conforming, non-stretching, hammocking heater. Additionally, the heater should be near the top surface of the mattress, in thermally conductive contact with the patient's skin, not buried beneath thick layers of foam or fibrous insulation.

Clearly, there is a need for conductive fabric heaters for use in therapeutic heated mattresses that are highly flexible, stretchable in at least one direction and durable without needing lamination to stabilize or protect the heater fabric. There is also a need for bus bar construction that does not result in thick, stiff, inflexible areas along the side edges of the heater. Then, maximally effective and safe therapeutic heated mattresses need to be designed using the stretchable, durable fabric heaters.

As known to those skilled in the art, modern surgical techniques typically employ radio frequency (RF) cautery to cut and coagulate bleeding encountered in performing surgical procedures. Every electrosurgical generator system may have an active electrode that is applied by the surgeon to the patient at the surgical site to perform surgery and an electrical return path from the patient back to the generator. The active electrode at the point of contact with the patient may be small in size to produce a high current density in order to produce a surgical effect of cutting or coagulating tissue. The return electrode, which carries the same current as the active electrode, may be large enough in effective surface area at the point of communication with the patient such that a low density current flows from the patient to the return electrode. If a relatively high current density is produced at the return electrode, the temperature of the patient's skin and underlying tissue will rise in this area and can result in a patient burn.

Return electrodes have evolved over the years from small 12×7-inch, flat stainless steel plates coated with a conductive gel that were placed under the patient's buttocks, thigh, shoulders, or any location where gravity could ensure adequate contact. The next development was flexible foam-backed electrodes. These flexible electrodes are about the same size as the stainless steel plates and are coated with a conductive polymer. They have an adhesive border so that they remain attached to the patient without the aid of gravity.

Described as early as 1938 and first introduced into the surgical market in 1960, capacitively coupled return electrodes offer an alternative to conductive return electrodes. Unlike conductive electrodes, which involve direct patient contact, a capacitively coupled electrode is placed close to, but not touching, the patient. It is separated from the patient by a dielectric barrier—that is, a layer of insulating material. This allows the electrode to form a capacitor with the patient. A capacitor is an electrical circuit element used to store a charge temporarily. In use, this type of electrode induces a current flow across the electrode-patient capacitor such that electricity is safely returned from the patient to the electrosurgical unit across a dielectric insulator layer, allowing the desired surgical effect at the surgical site.

A capacitively coupled return electrode consists of a single conductive plate, fabric or film that is encased in a dielectric material. The insulating material does not permit the charge to flow through the electrode to the patient. When placed in close proximity to each other, the conductive plate and the patient become capacitively coupled. Their separation is maintained by the electrode's insulating material, which forms a dielectric barrier between them. For example, a large flat sheet of conductive material that covers a portion of the operating table may be the electrode and the dielectric barrier may consist of plastic film, linens, cushions or other materials that may be placed between the patient and the electrode.

When the active electrode is applied at the surgical site, the electrosurgical unit induces an oscillating radio frequency (RF) voltage through the surgical site and between the patient and the return electrode's conductive plate. As this occurs, several events take place simultaneously. First, an electrical charge accumulates and diminishes in cycles, both on the surface of the patient overlapping the return electrode and on the electrode's capacitive plate, in equal and opposing polarities. Second, the dielectric material becomes polarized: an electrical charge will not move through it. Finally, as the electrical charge moves to and from the surface of the patient's skin, there is a loss of energy that produces a minimal amount of heat within the skin (as happens with a conductive return electrode).

If the dielectric is thin, meaning that the patient and the return electrode are close together—for example less than 2 mm—the capacitive coupling is very efficient. If the distance between the patient and the electrode increases, the efficiency of the coupling decreases. Therefore, minimizing the distance between the patient and the electrode may be desirable. The ability of this design to minimize the distance of both the heater and the grounding electrode from the patient may be particularly desirable with small pediatric patients who have minimal surface area contacting the support surface.

There is some concern that an unnoticed, accidental hole in the electrode's dielectric material could provide a conductive contact with the patient over a very small area, causing a large concentration of current to flow in a small area and to burn the patient. In some cases, thick layers of "self-sealing" gel material have been interposed between the electrode and the dielectric material to prevent a conductive pathway from occurring in the event of a hole in the dielectric material. The gel material is heavy and cumbersome.

Capacitive coupling electrodes generally have been mattress overlays, which are inconvenient, involving extra cleaning. Additionally, they are usually non-stretching conductive fabric—for example, woven nylon embedded into a heavy, cumbersome gel pad—which reduces the effectiveness of the pressure-reducing mattress of the surgical table. The conductive silver coating on the fabric electrode also diminishes radiolucency to x-rays, causing x-rays that are shot through the mattress to be grainy or distorted.

The location of the capacitive coupling grounding electrode under the patient is in direct competition for space with heated underbody warming pads and mattresses commonly used in surgery. Heated underbody warming pads and mattresses also work optimally when in close contact with the patient's skin. Therefore, both of these safety technologies may not perform optimally when used simultaneously as two separate devices since seemingly only one or the other can be optimally placed adjacent the patient's skin.

SUMMARY

There is a need for improvement in both heated underbody warming systems and electrosurgical grounding systems. The improvement described herein combines the capacitive coupling electrode with the heated underbody warming system. However, simply combining the two technologies into a single shell could produce a laminated structure that would be less stretchable, less flexible and less accommodating—further preventing the patient from sinking optimally into the support mattress and increasing the risk of pressure ulcers.

Combining the capacitive coupling electrode with the heated underbody warming system in a single layer of stretchable, flexible material that can serve as a heating element and grounding electrode simultaneously would prevent the problems resulting from a two-layer laminate structure and would reduce the cost and complexity of manufacturing.

Various embodiments include flexible and conformable heated underbody supports including mattresses, mattress overlays and pads for providing therapeutic warming to a person, such as to a patient in an operating room setting. In various embodiments, the heated underbody support is maximally flexible and conformable allowing the heated surface to deform and accommodate the person without reducing the accommodation ability of an under-laying mattress, for example.

In some embodiments, the underbody support includes a grounding electrode for electrosurgical equipment. These capacitive coupling grounding electrodes are well known in the arts. In some embodiments, the capacitive grounding electrode is the conductive heating element material that is simultaneously incorporated into the circuits of both the heater/power supply/controller and the electrosurgical unit. In some embodiments, the simultaneous use of the heating element material for heating and grounding allows both technologies to be positioned optimally close to the patient's skin for the maximum efficiency of each therapy.

In some embodiments the grounding electrode is the heating element. The heating elements of the instant inventions are preferentially made of conductive or semi-conductive fabrics or films. The conductive or semi-conductive properties of the heating element material allow it to double as a grounding electrode. The heater/grounding electrode may advantageously be made of a semi-conductive polymer such as polypyrrole. It is well known that the electrical properties of polypyrrole make it a suitable material for absorbing radar. Polypyrrole has been used as a radar absorbing material in "stealth" aircraft and watercraft. The microwave frequencies of radar are not unlike the RF frequencies used in electro-surgery. The semi-conductive properties of polypyrrole that lead to preferential absorption of high frequency electro-magnetic waves are in contrast to electrically conductive properties of composites made from powdered or vaporized carbon or metals. Metal powder particles deposited on the surface of a fabric material may conduct electricity, but do not preferentially absorb high frequency EM waves. Thin metal coatings may allow "tunneling" of some of the EM waves through the spaces between the particles, allowing the waves to pass right through the material without being absorbed. If the metallic coating is thick, "tunneling" may be prevented, but then reflection and scattering of the EM waves may result in decreased absorption. Therefore, the silver-coated fabrics that have been used in many past electrosurgical grounding pads are seemingly not preferential RF energy absorbers. A semi-conductive polymer such as polypyrrole is advantageous in that it is a preferential RF energy absorber.

Polypyrrole can be polymerized onto fabric and in the process coat each individual fiber, retaining the flexibility and stretchability of that fabric. The polymerization process results in a bond between the fiber and the polymer that is inseparable. This is in contrast to electrically conductive composites made from powdered or vaporized carbon or metals that may be applied to the surface of relatively non-stretching fibers and fabrics such as woven nylon, because such coatings will flake off with repeated flexion and stretching. Polypyrrole is, therefore, a preferable conductive material for heaters and grounding electrodes that are to be positioned under a patient because it allows flexion and stretching so that the patient can sink optimally into the support surface below the heater and/or grounding electrode.

In other embodiments, the grounding electrode is a separate layer of material positioned near and parallel to the heating element. In this case, the grounding electrode may advantageously be made of a semi-conductive polymer such as polypyrrole irrespective of what the material is used for the heating element.

In some embodiments, the grounding electrode is a separate layer of material, and there is no heater. In these cases, the grounding electrode may advantageously be made of a semi-conductive polymer such as polypyrrole.

In some embodiments, the grounding electrode wire is connected directly to the grounding electrode (heating element) material. This connection works acceptably as long as the grounding electrode is made of highly conductive material such as silver-coated nylon fabric. The very low resistance to flow through the silver-coated fabric allows the grounding wire to be connected to the electrode in any location.

In some embodiments, the grounding electrode wire is connected to one of the heating element bus bars. Connecting the grounding wire to the bus bar is advantageous when the grounding electrode material is a resistive heater material that adds resistance to the circuit. A grounding wire connected to one end of the heating element, rather than to a bus bar, would create a situation wherein the electrical resistance to current flow would be significantly greater for current originating at the far end of the heating element compared to current originating at the end of the patient closest to the wire connection. This situation would cause more of the current to flow through the parts of the patient closest to the wire connection and possibly create an unsafe condition. In contrast, since the bus bar runs substantially parallel to the long axis of the patient, along an edge of the grounding electrode, the distance from the bus bar to the patient is relatively equal along its length, and the resistance to the current flow caused by the heating element material is thus substantially equal along the entire length of the patient that is contacting the grounding electrode, creating a safe condition.

In some embodiments, the output electrical currents of both the heater/power supply/controller and the electrosurgical generator are "floating," meaning that they are not referenced to earth (ground) and have no electrical potential to earth (ground) or to each other. In some embodiments, the output electrical currents of both the heater/power supply/controller and the electrosurgical unit are "isolated," meaning that they have no electrical potential to and are not referenced to earth (ground). In some embodiments, the output electrical current of the heater/power supply/controller is a direct current. In some embodiments, the output electrical current of the heater/power supply/controller is low voltage, meaning equal to or less than 48 volts DC.

In some embodiments, the temperature sensor of the heated underbody warming system is located on the heating element, so that it senses the temperature of the heater in contact with the patient. The temperature sensor thus also serves as a safety sensor, decreasing power to the heater excess heat buildup under the patient from the electrosurgical grounding. The heater controller will alarm if the heater temperature exceeds a safe temperature for heating the skin whether the heating is due to the effect of the heater or the capacitive grounding.

In some embodiments, one or both sides of the heater material is coated with a thin layer of flexible, stretchable elastomeric material such as rubber or silicone. Preferably the elastomeric material is stretchable, flexible, self-sealing and protects the individual fibers of the heater material from moisture damage. This coating of elastomeric material interposed between the electrode and the dielectric material layers serves as second, redundant dielectric layer should an inadvertent hole be put into the outer shell. The redundant dielectric layer would prevent direct electrical coupling between the patient and the electrode material that could cause a burn.

In some embodiments, the heater/grounding electrode is encased in a flexible dielectric shell that can be flexed up along the sides of the small pediatric patient to improve both the heat transfer and capacitive coupling effects. Flexing the heater/grounding electrode places more of the surface area in close contact with the patient's skin for optimal performance of both heat transfer and capacitive grounding.

In some embodiments, the heated underbody support includes a heater assembly and a layer of compressible material. The heater assembly may include a heating element including a sheet of conductive fabric having a top surface, a bottom surface, a first edge and an opposing second edge, a length, and a width. The conductive fabric may include threads that are separately and individually coated with an electrically conductive or semi-conductive material, with the coated threads of the fabric being able to slide relative to each other such that the sheet is flexible and stretchable. The heater assembly may also include a first bus bar extending along the first edge (e.g., may be the entire first edge) of the heating element and adapted to receive a supply of electrical power, a second bus bar extending along the second edge (e.g., may be the entire second edge) of the heating element, and a temperature sensor. The layer of compressible material may be adapted to conform to a person's body under pressure from a person resting upon the support and to return to an original shape when pressure is removed. It may be located beneath the heater assembly and may have a top surface and an opposing bottom surface, a length, and a width, with the length and width of the layer being approximately the same as the length and width of the heater assembly.

In some embodiments, the conductive or semi-conductive material is polypyrrole. In some embodiments the compressible material includes a foam material and in some embodiments it includes one or more air filled chambers. In some embodiments, the heated underbody support also includes a water resistant shell encasing the heater assembly, including an upper shell and a lower shell that are sealed together along their edges to form a bonded edge, with the heater assembly attached to the shell along one or more edges of the heater assembly. In some embodiments, the heated underbody support also includes a water resistant shell encasing the heater assembly, including an upper shell and a lower shell that are sewn together along their edges to form a sewn and bonded edge. In some embodiments, the heating element has a generally planar shape when not under pressure, is adapted to stretch into a 3 dimensional compound curve without wrinkling or folding while maintaining electrical conductivity in response to pressure, and to return to the same generally planar shape when pressure is removed.

In some embodiments, the heating element includes a fabric coated with a conductive or semi-conductive material, which may be a carbon fiber or metal containing polymer or ink, or may be a polymer such as polypyrrole. In some embodiments, the heated underbody support also includes a shell including two sheets (e.g., layers, two sheets may be formed form one sheet folded over to form the two sheets or layers) of flexible plastic film or fiber reinforced plastic film with the two sheets sealed together near the edges of the heater assembly. In some embodiments, the heated underbody support also includes a power supply and a controller for regulating the supply of power to the first bus bar. In some embodiments, the power supplied by the power supply is floating, meaning that it does not have potential to ground or to other equipment. In some embodiments, the power supplied by the power supply is isolated, meaning that it does not have potential to ground. In some embodiments, the power supplied by the power supply is a low voltage, meaning that it is less than 48 volts. In some embodiments, the power supplied by the power supply is a direct current.

In some embodiments, the compressible material comprises one or more flexible air filled chambers. In some embodiments, the compressible material is a foam material. The heater assembly may be attached to the top surface of the layer of compressible material. In some embodiments, the heated underbody support includes a water resistant shell encasing the heater assembly and having an upper shell and a lower shell that are sealed together along their edges to form a bonded edge. In some embodiments, one or more edges of the heater assembly may be sealed into the bonded edge. In some embodiments, the heater assembly is attached to the upper layer of water resistant shell material. In some embodiments, the heater assembly is attached to the shell only along one or more edges of the heater assembly. In some embodiments, the heated underbody support also includes an electrical inlet, wherein the inlet is bonded to the upper shell and the lower shell and passes between them at the bonded edge.

In some embodiments, the temperature sensor is adapted to monitor a temperature of the heating element and is located in contact with the heating element in a substantially central location upon which a patient would be placed during normal use of the support.

Electrically heated mattresses are compressible and accommodating, thus the patients sink into the mattress and more body surface area is recruited to help support the weight of the patient. If the proper foam materials are chosen, virtually the entire posterior surface of the patient contacts the mattress. However, even with the added contact surface area, these mattresses are incapable of transferring enough heat to maintain patient normothermia, especially in pediatric patients.

The limitation in heat transfer is related to the fact that even though the entire posterior surface of the patient may be in contact, the surface geometry of the mattress prevents mattress contact with the surface areas of the patient's sides. As the patient sinks into the foam mattress, the upper layer of the protective shell material and the heater layer create a "hammock" effect. Sinking into foam with these materials on the upper surface creates an indentation with gradually tapered sides rather than the steeply tapered sides that would be preferable for conductive thermal contact. It is physically impossible for a foam mattress with a plastic film cover to closely engulf a patient. The foam and over-lying heater layer adjacent the side of the patient, will inevitably be tapering away from the patient. Thus, even though the patient may have sunken into the foam, only a small additional surface area along their posterior sides was gained for thermal contact.

Small pediatric patients have another problem with accommodation into the foam. Their light weight prevents them from sinking into the foam mattress. Therefore expecting the depression into the foam caused by the patients weight to form the foam around the patient's body thereby increasing the contact with their side surfaces, is clearly impossible in pediatrics.

There is a need for a surgical patient warming mattress that has a greater heat transfer capacity. Since the contact temperature cannot be increased without causing burns, seemingly the only option to increase heat transfer is to increase the body surface contact area. The increase the body surface contact area also increases the efficiency of the capacitive coupling of the grounding electrode in the mattress. The instant invention effectively increases the body surface contact area by substantially separating the patient support functions of the mattress from the patient warming and electrosurgical grounding functions of the mattress. By separating these two functions, each can be maximized independently. At the same time, both of the functions are still simultaneously maintained, to provide a safe and effective heated support surface for surgery.

In some embodiments, the heated underbody support may also include one or more additional inflatable chambers positioned under the layer of compressible material, with each of the inflatable chambers being elongated, having a longitudinal axis and being positioned side-by-side one another with their longitudinal axes extending substantially from the first end to the second end of the support. In some embodiments, the inflatable chambers can be inflated and deflated in two groups while the support is in use, with the inflatable chambers being in alternating groups such that each inflatable chamber is in a different group from each inflatable chamber which is beside it.

In some embodiments, the heated underbody support includes a plurality of additional inflatable chambers. In some embodiments, the inflatable chambers can each be inflated and deflated independently while the support is in use. In some embodiments, the inflatable chambers can all be inflated and deflated simultaneously as a group while the support is in use. In some embodiments, the inflatable chambers can all be inflated and deflated in two or more groups while the support is in use.

In some embodiments, the inflatable chambers are controlled by measuring and controlling the air pressure within the chambers. In some embodiments, the inflatable chambers are controlled by measuring and controlling the air volume within the chambers.

Some embodiments include methods of warming a person using any of the heated underbody supports described herein. In some embodiments, the method includes positioning the person on the heated underbody support, activating the support, and directing the support to maintain a desired temperature. Simultaneously, the underbody support may serve as the capacitive grounding electrode for the electrosurgical unit.

BRIEF DESCRIPTION OF THE DRAWINGS

FIG. 3 is an illustration of a heater assembly in accordance with embodiments of the invention.

FIG. 7 is a cross sectional view of a heated mattress overlay or pad in accordance with embodiments of the invention.

FIG. 8 is a cross sectional view of a heated mattress overlay or pad in accordance with embodiments of the invention.

FIG. 9 is an illustration of a heated mattress overlay or pad in accordance with embodiments of the invention.

FIG. 17 is a cross sectional view of a heated mattress overlay or pad with a power entry assembly located in the peripheral bond between the shell layers in accordance with embodiments of the invention.

FIG. 21 is a cross sectional view of a heated mattress including plurality of inflatable chambers in accordance with embodiments of the invention.

FIG. 22 is a cross sectional view of a heated mattress including a plurality of inflatable chambers in accordance with embodiments of the invention.

DETAILED DESCRIPTION

Figure 1:
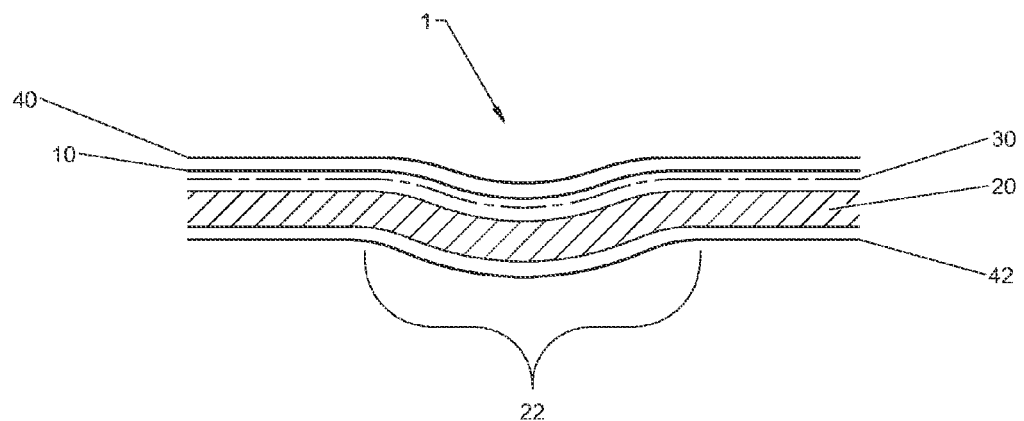
FIG. 1 is a cross sectional view of a heater assembly undergoing deformation in accordance with embodiments of the invention.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the embodiments of the invention. Those skilled in the art will recognize that many of the examples provided have suitable alternatives that can be utilized.

Embodiments include heated underbody supports which include heated mattresses, heated mattress overlays, and heated pads. The term underbody support may be considered to encompass any surface situated below and in contact with a user in a generally recumbent position, such as a patient undergoing surgery, including heated mattresses, heated mattress overlays and heated pads. Heated mattress overlay embodiments may be identical to heated pad embodiments, with the difference being whether or not they are used on top of a mattress. Furthermore, the difference between heated pad embodiments and heated mattress embodiments may be the amount of support and accommodation they provide, and some pads may be insufficiently supportive to be used alone like a mattress. As such, the various aspects which are described herein apply to mattresses, mattress overlays and pad embodiments, even if only one type of support is shown in the specific example.

In general, various embodiments described herein improve patient warming effectiveness by increasing accommodation of the patient into the heated mattress, mattress overlay, or pad, in other words, by increasing the contact area between the patient's skin and the heated surface of the mattress or mattress overlay. A heating element, and foam or air bladders of the mattress, which may also be included, are easily deformable to allow the patient to sink into the mattress, mattress overlay, or pad. This accommodation increases the area of the patient's skin surface in contact with the heated mattress, mattress overlay, or pad and minimizes the pressure applied to the patient at any given point. It also increases the surface contact area for heat transfer and maximizes blood flow to the skin in contact with the heat for optimal heat transfer. The accommodation of the patient into the mattress, mattress overlay, or pad is not hindered by a stiff, non-conforming, non-stretching, hammocking heater. Additionally, in various embodiments, a heating element is at or near the top surface of the underbody support, in thermally conductive contact with the patient's skin, not located beneath thick layers of foam or fibrous insulation.

Various embodiments further provide improved safety. For example, some embodiments provide a heating element that does not produce or reduces "pressure points" against the patient's body, such as against bony prominences, which can occur when a heater is stiff.

In certain embodiments, a heater assembly includes a heating element made of a conductive material. The conductive material may be stretchable in at least one direction or, alternatively, in at least two directions. One way to create a stretchable fabric heating element is to coat a conductive material onto individual threads or fibers of a carrier fabric. The threads or fibers may then be woven or knitted, for example, into a stretchable fabric. Other examples of conductive fabrics which may be employed by embodiments of the present invention include, without limitation, carbon fiber fabrics, fabrics made from carbonized fibers, and woven or non-woven substrates coated with a conductive material, for example, polypyrrole, carbonized ink, or metalized ink.

In some embodiments to be discussed, a conductive material may be applied to the fibers or threads before they are woven or knit into a fabric. In this way, the coated threads can move and slide relative to each other as the fabric is stretched, and can return to their original orientation when the stretching is stopped such that the fabric can return to its original shape. Alternatively, the conductive materials that coat the individual fibers in the fabric may be applied after the fabric is woven or knit using a dipping, spraying, coating or polymerization process or combinations thereof. A conductive polymer can be selected that coats the individual threads without bonding then together such that the threads remain able to slide relative to each other.

Types of materials which may be used for the fabric base include natural and synthetic materials such as polyurethane-polyurea copolymer (for example spandex or Lycra® made by INVISTA, Wichita, Kans.), polyester, polyamide, (for example nylon) or combinations thereof. Preferably the material is elastic in nature such that the threads or fibers can stretch and then return to their original size or length. Alternatively or additionally, stretch and elasticity may be provided by the manner in which the treads or fibers are knit or woven, such as by forming a twill weave. Alternatively or additionally, stretch and elasticity may be provided by the manner in which fibers or groups of fibers are twisted or combined prior to being knit or woven into fabric. Alternatively, or additionally the stretch and elasticity may be provided by the structure introduced to the fabric through embossing, creping or other mechanical means. Alternatively or additionally stretch and elasticity may be provided by the use of stretchable polymer or fibers in a nonwoven fabric.

The conductive coating may be applied to the individual fibers or threads before forming a fabric by spraying, coating or dipping, for example. Various conductive materials may be used. Examples include conductive and semi-conductive polymers include polypyrrole, polyaniline and polyacetylene.

In some embodiments, in contrast to non-stretchable conductive film heaters, where a carbon (or other conductive material) impregnated plastic film is extruded onto or bonded onto a base layer such as a fabric base layer, the preferred heating element material has a conductive or semi-conductive material coated onto the individual threads or fibers of the carrier fibers prior to weaving or knitting into a fabric. This maintains the natural flexibility and stretchability of the fabric rather than turning the fabric into a non-stretchable fiber reinforced film.

The conductive or semi-conductive coating comprises a polymer and is bound as a layer surrounding the individual threads or fibers by a process of polymerization. Polymerization results in a very secure bond. The flexible coating on each individual thread or fiber preferably does not crack, fracture or delaminate during flexion. Polymerization of these conductive or semi-conductive materials onto individual fibers of the carrier fabric is a preferable process for producing a durable, flexible and stretchable heater assembly. Semi-conductive polymer coatings such as polypyrrole are preferred for this invention, however, other coating processes are anticipated and conductive coatings that use carbon or metal as the conductive material are also anticipated.

The electrically conductive or semi-conductive fabric heater materials used in heating elements is preferably highly flexible and durable such that neither the carrier fiber nor the semi-conductive polymer coating will fracture with repeated flexing, loading and stretching. Additionally, the conductive or semi-conductive fabric heating element of embodiments of this invention does not require lamination between layers of plastic film for protection or stabilization, though it may be laminated if desired.

The conductive fabric heating element material may be highly flexible and conformable, allowing the heated surface to comfortably deform and accommodate the patient. To accomplish this, the heater assembly may be a flexible, electrically conductive fabric heating element that may be made of woven or knit fabric that can preferably stretch in at least one direction. The fabric heating element may be durable without requiring lamination between plastic film sheets for stabilization and protection, though in some embodiments the heating element may be laminated. In some embodiments, the flexible and conformable fabric heating element can be included in a mattress overlay and can be positioned directly against the plastic film of an upper surface of a mattress with which it is used without requiring a foam pad there between, or alternatively a foam pad may be included beneath the heating element. Furthermore, with no foam or thermal insulation layer between the heating element and the patient, heat transfer from the heating element to the patient is maximized.

The heating element may include a flexible flat sheet of the conductive material. In some embodiments, it is rectangular having opposing first and second edges and opposing third and fourth edges extending from the first to second ends, a first planar surface and an opposing bottom planar surface. According to preferred embodiments of the present invention, the heating element also includes closely spaced conductive elements such that the heating element has a substantially uniform Watt density output, in some embodiments less than approximately 0.5 watts/sq. inch, and, preferably, between approximately 0.1 and approximately 0.4 watts/sq. inch, of one or both surfaces, across a portion of or the entirety of the surface including and extending to the edges of the heating element. The closely spaced elements can be conductive threads woven into the fabric or conductive materials such as conductive ink applied to the fabric.

According to an exemplary embodiment to be described herein, a conductive fabric comprising the heating element comprises woven polyester fibers individually coated with polypyrrole (available from Eeonyx Inc., Pinole, Calif.). The coated fabric may have an average resistance, for example, determined with a four point probe measurement, of approximately 15-20 ohms per square inch at about 48 volts, which is suitable to produce the preferred Watt density of approximately 0.1 to approximately 0.4 watts/sq. in. for the surface of the heating element, when the heating element has a width between the bus bars in the neighborhood of about 16-28 inches, though wider and narrower heater element widths are also contemplated. Such widths are suitable for a mattress, mattress overlay, or pad heating assembly, some embodiments of which will be described below. The resistance of such a conductive fabric may be tailored for different widths between bus bars (with wider involving a lower resistance and narrower involving a higher resistance) by increasing or decreasing a surface area of the fabric that can receive the conductive coating, for example, by increasing or decreasing the basis weight of the fabric. Resistances over surface areas of conductive fabrics such as these may vary, for example, due to variation in a thickness of a conductive coating, variation within the conductive coating itself, variation in effective surface area of the substrate which is available to receive the conductive coating, or variation in the density of the substrate itself. Local surface resistance across a heating element is directly related to heat generation according to the following relationship: Q (Joules)=$I^2$ (Amps)×R(Ohms). Variability in resistance thus translates into variability in heat generation, which is measured as a temperature. Precise temperature control can be maintained in embodiments which are employed to warm patients undergoing surgery, for example.

The stretchable fabric heating element is able to deform in response to a focal pressure applied to the surface of the fabric, into a smooth 3-dimensional compound curve without wrinkling or folding. A smooth compound curve cannot be formed out of non-stretchable fabrics or films. The stretchable fabric heating element preferably also exhibits elastic properties that allow it to revert to its original planar shape when the deforming pressure is relieved. The fabric heating element can be provided with appropriate tensile properties such that the amount of stretch, or strain, as appropriate to prevent hammocking and allow accommodation of the patient into the heated mattress or mattress overlay does not result in stresses that exceed the elastic limit of the material. In some embodiments, for example, an increase in the width of a 20 inch wide mattress or mattress overlay of approximately one inch during stretching achieves the desired goals without exceeding the elastic limit of the stretchable fabric heating element or introducing permanent plastic deformation.

In an illustrative embodiment, an example of a heater assembly 1 including a stretchable fabric heating element 10 is shown in FIG. 1, which depicts a cross section of a portion of the heater assembly 1. This example includes a heating element 10, a foam layer 20 beneath the heating element 10 and bonded to the heating element 10 by a layer of adhesive 30. The heater assembly 1 also includes an upper shell 40 and a lower shell 42. The heater assembly 1 curves smoothly under pressure from the weight of a patient's body (not shown) to stretch into an area of compound curve deformation 22.

In the embodiment shown in FIG. 1 and in several other embodiments, a foam layer 20 is included beneath the heating elements 10. However, the foam layer 20 may alternatively be described as a layer of compressible material in each of these embodiments and is not limited to foam. For example, the layer of compressible material may comprise gel, stuffing material such as polyester, polyester pellets, bean bag material such as polystyrene beads, air filled compartment, or any material that provides a flexible layer for patient accommodation.

Heat transfer is maximized when the heating element 10 is in conductive thermal contact with the patient. However, in some embodiments, at least one layer of plastic film is interposed between the heating element 10 and the patient to protect the heating element 10. One or more layers of thin plastic film may form an upper film 40 between the heating element 10 and the patient to introduce minimal thermal resistance to heat flow. In certain embodiments of this invention the fabric heating element 10 may be laminated between two layers of thin (<0.004 in.) and preferably stretchy (e.g. urethane or polyvinyl chloride) plastic films 40, 42. Laminating a thin layer of plastic film directly onto each side of the heating element 10 forming the upper and lower shell 40, 42 protects the heating element 10 fabric from damage by liquids and oxidation. Thin layers of plastic film 40, 42 are sufficient to protect the heating element 10 from liquid and gases, add minimal if any stiffness to the construction, and still allow the heating element 10 to stretch and return to its original shape. This is in contrast to some other conductive fabrics which may require lamination between two thick layers of plastic film in order to provide structural strength and durability, resulting in a stiff and non-stretchable heater.

In some embodiments, the heating element is coated with one or more thin layers of elastomeric materials such as rubber or silicone. The layers of elastomeric material protect the heating element 10 material from damage due to moisture and oxidative chemicals such as hydrogen peroxide.

The layers of elastomeric material may also provide an electrically insulating layer over the heating element 10 material. In some embodiments, the heating element 10 doubles as a grounding electrode. If the heating element 10 is also used as the grounding electrode during electrosurgery, the upper layer of elastomeric material (e.g. 40) forms a second dielectric layer between the patient and the heating element 10, adding to the safety of the heater assembly 1 should the outer shell material 40, 42 be cut or pierced. The second dielectric layer (e.g., 40) prevents a direct electrical contact between the patient and the grounding electrode (e.g., 10).

The pressure relief provided by the underbody support is maintained by allowing maximal accommodation (allowing the patient to sink into the support) without the heater creating a "hammocking" force. By allowing maximal accommodation and avoiding hammocking, cutaneous blood flow is maximized at the pressure points, which minimizes the risk of pressure ulcers. The pressure needed to collapse capillaries is said to be 12 to 32 mm Hg. By allowing maximal accommodation and avoiding hammocking, cutaneous blood flow is generally maximized. By maximizing blood flow, the ability of the skin and tissue to absorb heat from the heating element 10 and transfer it to the rest of the body is also maximized. Further, by allowing the patient to sink into the underbody support (accommodation), the surface area of the heater assembly 1, in contact with the patient is maximized and thus heat transfer is maximized. In other words, the surface area of the heating element in thermal communication with the patient is maximized and thus heat transfer is maximized.

Figure 2:
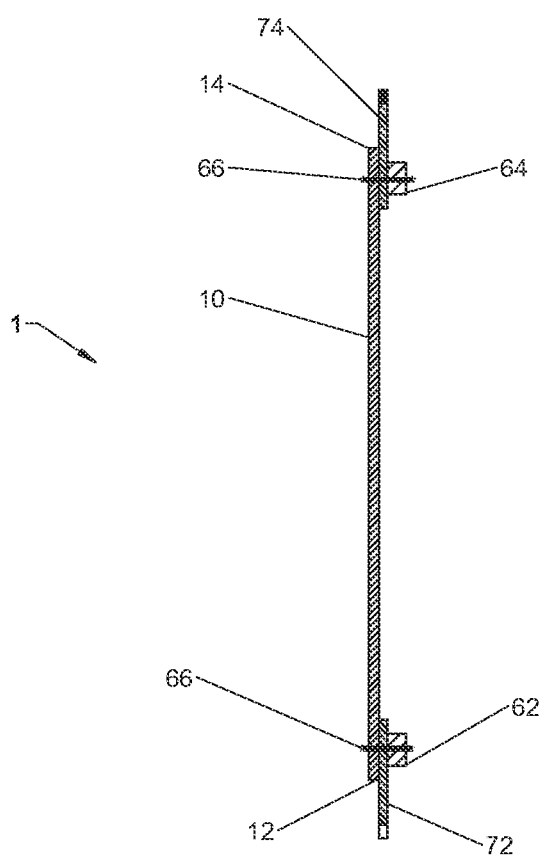
FIG. 2 is a cross sectional view of a heater assembly in accordance with embodiments of the invention.

In certain embodiments of the invention as in FIGS. 2 and 3, the conductive or semi-conductive fabric heating element 10 is made into a heater assembly 1 by attaching two electrical conductors, or bus bars 62, 64 along opposing edges of the fabric heating element 10. The bus bars 62, 64 of some embodiments of this invention may be attached to the heating element 10 material by sewing with electrically conductive thread 66. This construction maintains flexibility and durability with repeated flexing. The sewn connection between the bus bar 62, 64 and the heating element 10 fabric according to embodiments of the invention results in a connection that is very robust, flexible and tolerant of extreme flexing and resistant to degradation.

According to some embodiments, the bus bars 62, 64 are coupled to the heating element 10 by a stitched coupling, for example, formed with electrically conductive thread such as silver-coated polyester or nylon thread (Marktek Inc., Chesterfield, Mo.), extending through the conductive fabric material and through the bus bars 62, 64. Alternative threads or yarns employed by embodiments of the present invention may be made of other polymeric or natural fibers coated with other electrically conductive materials. In addition, nickel, gold, platinum and various conductive polymers can be used to make conductive threads. Metal threads such as stainless steel, copper or nickel could also be used for this application. According to an exemplary embodiment, the bus bars 62, 64 are comprised of flattened tubes of braided wires; for example, a flat braided silver coated copper wire, and may thus accommodate the attaching thread extending there through, passing through openings between the braided wires thereof. In addition, such bus bars 62, 64 are flexible, thereby enhancing the flexibility of the mattress heater assembly 1. According to alternate embodiments, the bus bars 62, 64 can be a conductive foil or wire, flattened braided wires not formed in tubes, an embroidery of conductive thread, a printing of conductive ink, or other suitable bus bar construction. Preferably, the bus bars 62, 64 comprise of a flat braided silver-coated copper wire material since a silver coating has shown superior durability with repeated flexion, and is less susceptible to oxidative interaction with a polypyrrole coating of the heating element 10. Additionally, an oxidative potential due to dissimilar metals in contact with one another is reduced if a silver-coated thread is used for the stitched coupling of a silver-coated bus bar.

FIGS. 2-3 depict a heater assembly 1 and a stitched bus bar construction according to embodiments of the invention. It includes a heating element 10, a first bus bar 62 at a first end 12 of the heating element 10 and a second bus bar 64 at a second end 14 of the heating element 10. A first insulating member 72 is located between first end 12 and first bus bar 62 and a second insulating member 74 is located between second end 14 and second bus bar 64. Conductive thread 66 connects the heating element 10 to the bus bars 62, 64 through the insulating members 72, 74. In this way, the electrical contact points between the bus bars 62, 64 and the heating element 10 may be solely defined by the conductive thread 66 of the stitched couplings.

Insulating members 72, 74 may be fiberglass material strips having an optional polytetrafluoroethylene (PTFE) coating and a thickness of approximately 0.003 inch, for example. Alternatively, electrically insulating members 72, 74 could be comprised of a polymeric film, a polymeric film reinforced with a fibrous material, a cellulose material, a glass fibrous material, rubber sheeting, polymeric fabric, polymeric or rubber-coated fabric or woven materials or any other suitable electrically insulating material.

The use of conductive thread stitches 66 of the coupling maintains a stable and constant contact with the bus bar 62, 64 on one side and the heating element 10 on the other side of the insulator 72, 74. Specifically, the stitches can produce a stable contact in the face of any degree of flexion, so that the potential problem of intermittent contact between the bus bar 62, 64 and the heating element 10 (that could arise in embodiments where the bus bar relies upon direct physical contact between the surface of the bus bar with the surface of the heating element) can be avoided. The stitching 66 comprises the electrical connection between the bus bar 62, 64 and the heating element 10, and by using a conductive thread that has a lower electrical resistance than the conductive fabric of the heating element 10, the thread does not generate heat under normal conditions. In addition to the heated mattress, mattress overlay, and pad applications described herein, such a design for providing for a uniform and stable conductive interface between a bus bar and a conductive fabric material can be used to improve the conductive interface between a bus bar or an electrode and a conductive fabric in non-flexible heaters, in electronic shielding, in radar shielding and in other applications of conductive fabrics.

In some embodiments, the stitched coupling between the bus bar 62, 64 and the heating element 10 comprises two or more rows of stitches 66 for redundancy and stability. In other embodiments, a single row may be used. The stitching 66 may extend along substantially the entire end 12, 14 of the heating element 10.

Various embodiments include heated mattresses, mattress overlays, and pads that automatically optimize both the safety and efficacy of the warming in multiple zones across the surface of the mattress, mattress overlay, or pad. The zones are differentiated by whether the mattress or mattress overlay is directly contacting the patient or is substantially not contacting the patient. In general, the central portion of the mattress or mattress overlay will be contacting the patient and the lateral edge portions will predominately not be contacting the patient. Therefore, the central region will transfer heat to the patient conductively and the lateral regions will transfer heat to the patient via radiation and natural convection. The location of the central contact zone is predictable because the patient is anesthetized and therefore, not spontaneously moving or rolling in bed.

Figure 5:
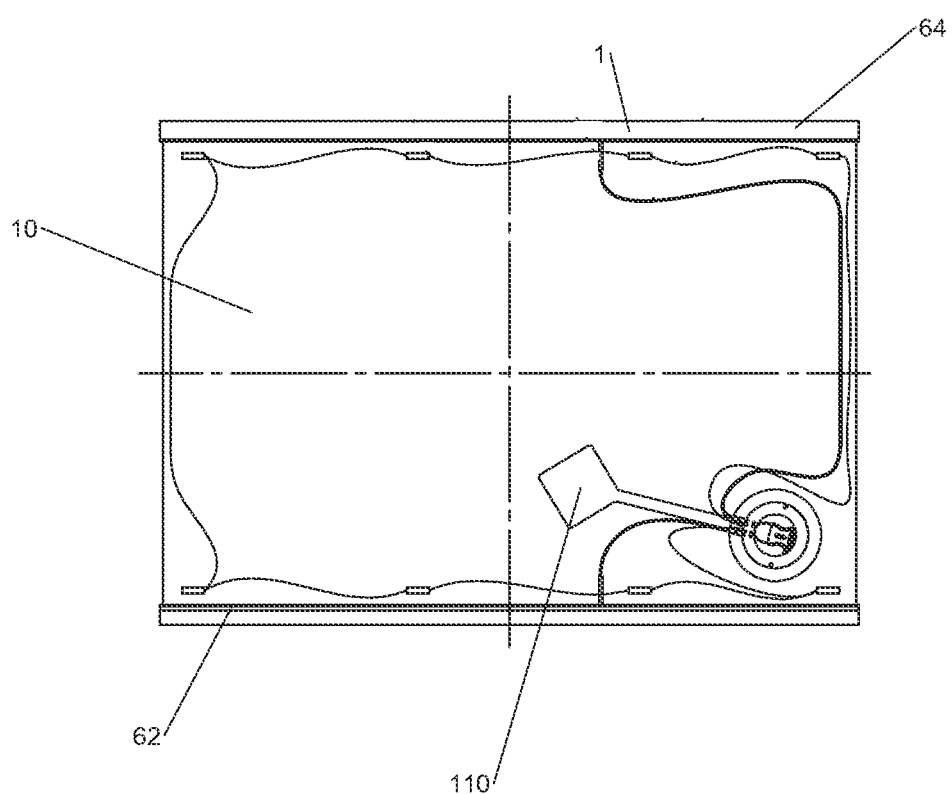
FIG. 5 is an illustration of a heater assembly in accordance with embodiments of the invention.

FIG. 5 is an aerial view of a heater assembly 1 for use in a heated underbody support according to embodiments of the invention. As shown in FIG. 5, the heating element 10 has a substantially uniform Watt density across its surface. Preferably, this is accomplished with a conductive fabric heating element 10 material. The central zone and the adjacent peripheral zones of the heating element 10 are powered by the same controller. A temperature sensor assembly 110, which inputs to the controller, is attached to the heating element 10 in a location which is predicted to be in direct conductive contact with the patient's body when the patient is positioned on the support—the central zone. Once the patient is in position on the support, the area of contact between the patient and the support (e.g. area of thermal communication between the patient and the heating element 10) defines a contact portion while the remaining area is the non-contact portion of the support. The central zone is therefore the portion of the heating element upon which a patient is positioned during normal use and is an estimate of where at least the contact portion is most likely to be. Locating the temperature sensor assembly in the central zone can be used to optimize the safety and efficacy of the warming mattress or mattress overlay. During use, in the central zone 10 where the temperature sensor assembly 110 is attached to the heating element 10, the top surface of the heated underbody support is in contact with the patient for effective conductive heat transfer. The patient described herein may, for example, be a $50^{th}$ percentile male, a $50^{th}$ percentile female, and/or $50^{th}$ percentile child. In some embodiments, the patient may cover the range of 0-$100^{th}$ percentile male, 0-$100^{th}$ percentile female, and/or a 0-$100^{th}$ percentile child or infant. In a preferred embodiment the patient may cover the range from a $5^{th}$ percentile infant to a $95^{th}$ percentile male. Another way of describing the patient may be a 165 pound person having a height of 5'8" tall.

For safety reasons, the temperature of the heating element 10 in the conductive zone or contact portion may be controlled to temperatures no greater than 38-40° C., for example. In the areas of contact between the patient and the mattress or mattress overlay, the patient's body can act as a heat sink and draw heat from the heating element 10. If the temperature sensor assembly 110 in that region senses the temperature of the support decreasing, it provides an input to the controller, and the controller responds by increasing the electrical power to the entire heating element 10. The temperature of the central zone of the heating element 10 may eventually reach—but not exceed—the set point. This assures optimal heat transfer as well as optimal safety in the contact portion which is the conductive heat transfer region.

Additionally, the conductive fabric heating elements 10 preferably have a low thermal mass. Therefore, if the peripheral portion of the heated underbody support that is operating at the higher temperature is touched, suddenly converting a non-contact zone into a contact zone, that part of the heating element 10 quickly cools to the safe operating temperature of the conductive central zone. The non-contact peripheral zones 14 of a heated underbody support may momentarily feel warm when contacted, but will cool to the lower temperature of the contact zone without transferring sufficient thermal energy to injure the patient. Thermal mass, or heat storing capacity, is commonly defined as the product of the mass and the specific heat of a material. Materials with a low specific heat, a low density, or a combination thereof, will exhibit a low thermal mass. For example, a polymer such as polyurethane, with a density of 1100 kg/m3 and a specific heat of 1.7 kiloJoules (kJ) per kilogram-degree Kelvin has a volumetric heat capacity of 1870 kJ/m3-° K, and foam can have a heat capacity of 20-200 kJ/m3-° K. A thin layer of polyurethane film covering a fabric heating element and a foam layer has significantly lower thermal mass than a water mattress, for example, given the volumetric heat of water of 4180 kJ/m3-° K. The thermal mass of a heated underbody support can therefore be reduced by using components that exhibit a low density and/or specific heat. In addition, reducing the thickness, or total volume of materials used in the shell, for example, will reduce the thermal mass of the heated underbody support. Various embodiments may be made with materials with low thermal mass such as films, fabrics and foams. Some embodiments do not incorporate materials such as thick pieces of metal, liquid water or water-based materials such as gels that have relatively high thermal masses.

In these embodiments, when the temperature sensor assembly 110 is attached to an area of the heating element 10 that is typically in conductive contact with the patient during normal use, any other area of the heating element 10 that is also in conductive contact with the patient will also be at or near the set point or desired temperature. The temperature differentiation and location of the zones is automatic and depends on whether or not there is conductive contact between the heating element 10 and the patient.

Figure 6:
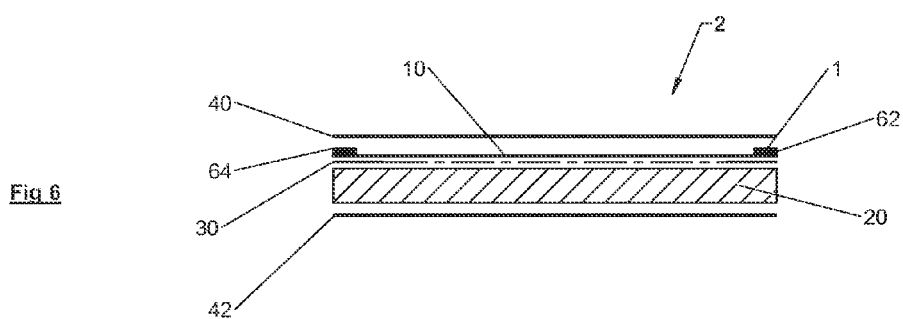
FIGS. 6, 6A and 6B are cross sectional views of heated mattress overlays or pads in accordance with embodiments of the invention.

When not stretched, fabric heating elements 10, as described herein, provide an even heat output or Watt density across their surface, unless they are folded or wrinkled, doubling or tripling the heating element 10 layers in the folded or wrinkled portion. The entire heating element 10 may have a relatively low Watt density, such as less than 0.5 watts per square inch, for example. Therefore, it is preferable to prevent local wrinkling of the heating element 10. An embodiment of a heated mattress overlay 2 including a heater assembly 1 and a foam layer 20 and having reduced wrinkling or folding is shown in FIG. 6. It should be noted, however, that whether a heater unit is described as a heated mattress, heated mattress overlay, or heated pad is largely unimportant, and most embodiments could be used variously as heated underbody supports. While a heated mattress overlay may have no layer of padding or may have a thinner layer of padding, a heated pad typically has padding that may be thin or thick, a heated mattress may have an even thicker layer of padding. As such, various embodiments may be used alone, in the manner of a mattress, or on top of a mattress, in the manner of a mattress overlay. Descriptions relating to heated mattress overlays therefore also apply to descriptions of heated mattresses and heated pads, and vice versa.

The mattress overlay 2 as shown in FIG. 6 includes a fabric heating element 10 with bus bars 62, 64 attached that is additionally attached to a layer of compressible material 20 by a layer of adhesive 30 beneath the heating element 10. To prevent wrinkling, the layer of compressible material 20 may be comprised of a simple urethane upholstery foam or its equivalent or one of the many "high tech" foams such as visco-elastic foams. Many foams are suitable for the layer of compressible material 20 but may be durable and able to prevent wrinkling of the heater during use, yet may also be flexible, stretchable and accommodating. In the embodiment shown, the mattress overlay 2 also includes an upper shell 40 and a lower shell 42 forming an outer shell that encases the heater assembly 1 and compressible material layer 20.

The compressible material layer 20 may be a single layer or may be a stack of materials that includes a layer of foam. This stack could include foam layers of different densities, different accommodation properties, different stiffness or different polymers. Additionally, the stack of materials can include other materials such as woven or non-woven fabrics or films, to achieve other characteristics such as lateral stiffness or durability and strength. The term compressible material layer 20 therefore refers generally to single layers of foam as well as multilayered stacks that include one or more layers of foam and may include other materials. Also, the layer of foam may alternatively be a layer of compressible material as described above.

As shown in FIG. 6, the attachment of the heating element 10 to the compressible material layer 20 may be achieved by adhesive bonding 30 across the entire interface between the two. The bond may be made with an adhesive comprising a pressure-sensitive adhesive without a reinforcing fiber or film carrier. Since the compressible material layer 20 is preferably flexible, stretchable and compressible, such a bonding made with such an adhesive does not alter the flexibility and stretch-ability of the heating element 10 or heated mattress overlay 2. Alternately, the heating element 10 may be attached to the compressible material layer 20 only along one or more of the edges 12, 14, 16, 18 such as along two opposing edges such as edges 12, 14, or in an intermittent pattern.

FIG. 7 depicts a cross section of a portion of an alternative embodiment of a heated mattress overlay 2, in which the fabric heating element 10 and the overlaying plastic film layer comprising an upper shell 40 include a layer of fabric or foam 74, inserted there between. The layer of fabric or foam 74 is preferably treated with manganese dioxide (MnO2) to act as a catalyst in the destruction of hydrogen peroxide cleaning fluid vapor that may permeate the upper shell material 40 and enter the shell where it can damage the electrical components.

An alternative embodiment is shown in the heated mattress overlay 2 which is shown in FIG. 8. In this embodiment, the fabric heating element 10 is anchored to a shell including an upper shell 40 and a lower shell 42 along its edges and thus held in an extended and wrinkle-free condition. Anchoring strips 46 comprised of plastic film or a suitable alternative are attached along the edges of the heating element 10, preferably by sewing to form a sewn connection 85, though other forms of attachment may be used such as adhesive bonding. The anchoring strips 46 extend along all four edges of the heating element 10 to form a peripheral bond 48. Alternatively, the anchoring strips 46 may extend along only one pair of opposing edges such as edges. The anchoring strips 46 may be made of the same material as the shells 40, 42, such as plastic film, and therefore can be bonded around the periphery of the mattress overlay 2, being sandwiched between and incorporated into the bond between the upper shell 40 and lower shell 42.

Since some embodiments maintain the heating element 10 in an extended and unwrinkled condition is preferable in order to avoid hot spots, more than one of these heating element 10 anchoring embodiments may be used simultaneously. To maintain flexibility, conformability and stretchability, the upper and/or lower shell 42, 44 may be adhered to the heating element 10 or the compressible material layer 20, across their broad surfaces as shown, for example, in FIG. 7, or may not be so adhered. However, in an alternate embodiment the heating element 10 can be bonded to the upper shell 40, for example. This may be advantageous for minimizing wrinkling of the heating element 10 or plastic film layer of the shell 40, 42.

Figure 10:
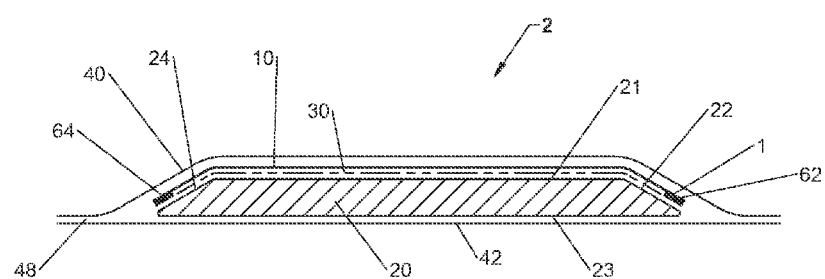
FIG. 10 is a cross sectional view of a heated mattress overlay or pad in accordance with embodiments of the invention.

Stretching the heating element 10 from the edges 12, 14 could result in hammocking of the heating element 10, such as if the mattress overlay 2 or pad is anchored tightly to the operating room table along the lateral edges. Various embodiments therefore include a beveled edge 22, 24 on the compressible material layer 20, as shown in FIG. 10, for example, to help prevent hammocking by creating a slight excess of heating element 10 material as the heating element 10 transitions across the angle between the upper surface 21 of the compressible material layer 20 and the beveled edge 24. Additionally, the angle also creates an area of compressible foam that can compress in response to the heating element 10 being deformed by a weight resulting in the heating element 10 pulling toward the center from the edges 12, 14. Rather than being stretched tight out to the edge as would occur with a non-beveled compressible material layer 20, thereby potentially forming a hammock, the heating element 10 moves toward the center by compressing the compressible material layer 20 at the angle between the upper surface 21 and the beveled edge 22, 24 of the foam layer 20, in response to deformation by a weight applied to the central area of the heated mattress or mattress overlay 2. In this way, the risk of hammocking is further reduced or eliminated.

The compressible material layer 20 (or layer of compressible material) supporting the heater assembly 1 in certain embodiments of this invention could be almost any thickness that is advantageous for the given application (for example, 0.5-6.0 inches). The compressible material layer 20 may be uniform in thickness and density or it may be contoured in thickness, shaped, scored or segmented according to areas of different densities.

FIG. 10 depicts a cross section of a heated mattress overlay 2 including a shaped compressible material layer 20 according to various embodiments. In this embodiment, the compressible material layer 20 is beveled or tapered along one or more edges, such as the edges that abut and support the bus bars 62, 64 which are attached to the compressible material layer 20 along the beveled edges 22, 24. The compressible material layer 20 is generally planar with an upper surface 21 and an opposing and lower surface 23. In some embodiments the lower surface 23 may be parallel, or partially parallel to the upper surface 21. In some embodiments, the beveled ends 22, 24 of the compressible material layer 20 are not perpendicular to the surfaces 21, 23 but rather angle inwardly, toward the upper surface 21. In a cross section perpendicular to the surface, the compressible material layer 20 may be trapezoidal in shape rather than rectangular, with the lower surface 23 forming the larger trapezoid base and the upper surface 21 forming the smaller trapezoid top. Alternatively, the lower portion of the edge could be perpendicular to the bottom surface while only the upper portion of the edge may be angled inwardly to form a bevel. Other embodiments including beveled edges are also anticipated.

Figure 11:
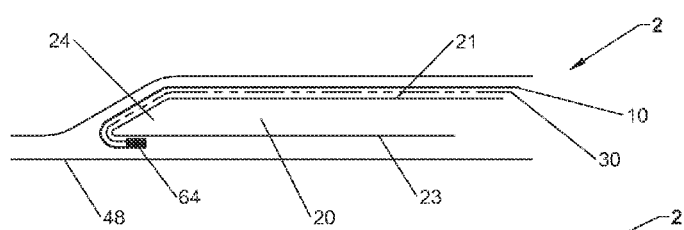
FIG. 11 is a cross sectional view of a heated mattress overlay or pad in accordance with embodiments of the invention.
Figure 12:
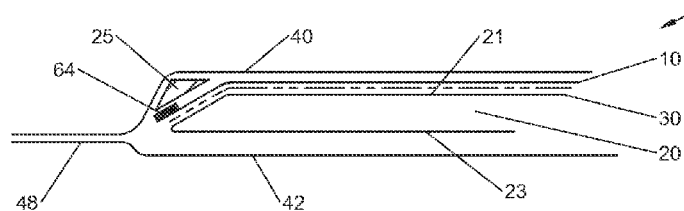
FIG. 12 is a cross sectional view of a heated mattress overlay or pad in accordance with embodiments of the invention.

The portions of the heating element 10 attached to the bus bars 62, 64 are preferably bonded to the compressible material layer 20 along the beveled ends 22, 24. Locating the bus bars 62, 64 on the beveled ends 22, 24 of the foam layer 20 provides some protection of the bus bars 62, 64 from mechanical stress when patients are sitting or lying on the underbody support 2. Alternatively, to provide additional protection to the bus bars 62, 64, the heating element 10 may be wrapped around the compressible material layer 20 and onto the bottom surface 23 so that the bus bars 62, 64 are located under the foam layer beveled ends 22, 24 and attached to the bottom surface 23 as shown in the cross section shown in FIG. 11, for example. In a further alternative shown in FIG. 12, the beveled piece of compressible material that is removed from the compressible material layer 20 or any other triangular or wedge shaped piece of compressible material of complementary size and shape to fit the space may be bonded over the bus bars 62, 64 of the heater assembly 1, along the beveled edges 22, 24 of the compressible material layer 20 to form a filler 25, to fill in the beveled space and protect the bus bars 62, 64. The compressible material filler 25 may be sized such that, when in place above the bus bars 62, 64, the horizontal upper surface 21 of the heated mattress overlay 2 (or other underbody support) above the central, non-beveled portion of the compressible material layer 20, is level with the horizontal upper surface 21 of the overlay 2 above the beveled end 24. In these embodiments the heating element 10 extends across the upper surface 21 of the compressible material layer 20, and the bus bars 62, 64 are away from and lower than the upper surface 21. In this way, the bus bars 62, 64 may be physically protected from damage by bonding them onto or beneath the beveled edges 22, 24 of the compressible material layer 20, where they are effectively recessed from the upper surface 21 of the foam layer 20. The beveled edges 22, 24 of the compressible material layer 20 allow the bus bars 62, 64 to be optionally covered with a compressible material filler 25 to act as a protective barrier in this location for added protection, without adversely affecting the look of the smooth top surface of the underbody support 2, thereby basically filling the bevel space with a compressible material filler 25 to create an overall rectangular cross sectional shape.

Figure 13:
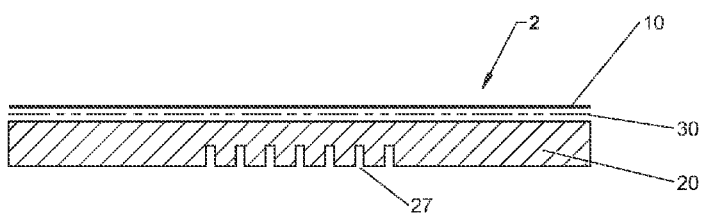
FIG. 13 is a cross sectional view of a heated mattress overlay or pad with partial thickness cuts or channels in the foam layer in accordance with embodiments of the invention.

In some embodiments, a portion of the compressible material layer 20 is thinned or scored in an area, from one lateral edge to the other of the area, with the area located to overlie the location of transition from one cushion of an operating table to the adjacent cushion under normal conditions of use. Preferably the thinning or scoring is on the bottom surface 23 of the compressible material layer 20 and therefore away from the patient contact top surface 21. Since operating room tables are designed to flex at this location between the operating table cushions, a thinned compressible material layer 20 at the location of transition between cushions will aid in flexion of the heating element 10 and reduce the chances of the heating element 10 wrinkling during flexion. Alternatively, the compressible material layer 20 could be scored or cut or otherwise have one or more gaps or channels completely through or partially through its thickness on the bottom surface 23 at the flexion locations or other areas where added flexibility may be desirable, as shown in FIG. 13, for example. In the embodiment shown, multiple small channels 27 are present in a portion of the compressible material layer 20 where the compressible material layer 20 is thinner. These channels 27 may extend across the compressible material layer 20, from one end to the opposing end, such as across the width or the length of the compressible material layer 20, such as in a direction parallel to and aligned with the transition between operating table cushions. In use, the underbody support 2 may be positioned over a table or bed with which it is designed to be used such that the channels are located over the flexion locations of the table or bed. The table or bed may then be adjusted by bending at a flexion point (such as to raise or lower a patient's upper body or legs by bending or extending the patient at his or her hips) and the compressible material layer 20 of the underbody support 2 can bend easily at this location due to thinness or scoring at the location of flexion, while the heating element 10 can likewise bend without wrinkling or folding due to its flexibility and elasticity.

In some embodiments, the compressible material layer 20 may be thinned or scored or have gaps or channels 27 longitudinally in order to increase flexibility for bending the heated underbody support 2 around a longitudinal axis such as a long axis of a body. This may be advantageous to aid in wrapping the heated underbody support 2 around a patient being positioned within a "bean bag" or "peg board" positioner. The longitudinal thinning or scoring or presence of gaps or channels 27 allows the heated underbody support 2 to be wrapped around the dependent portion of the patient, increasing the area of surface contact between the heating element 10 and the skin while avoiding wrinkling of the heating element 10 due to the bending of the compressible material layer 20.

Figure 14:
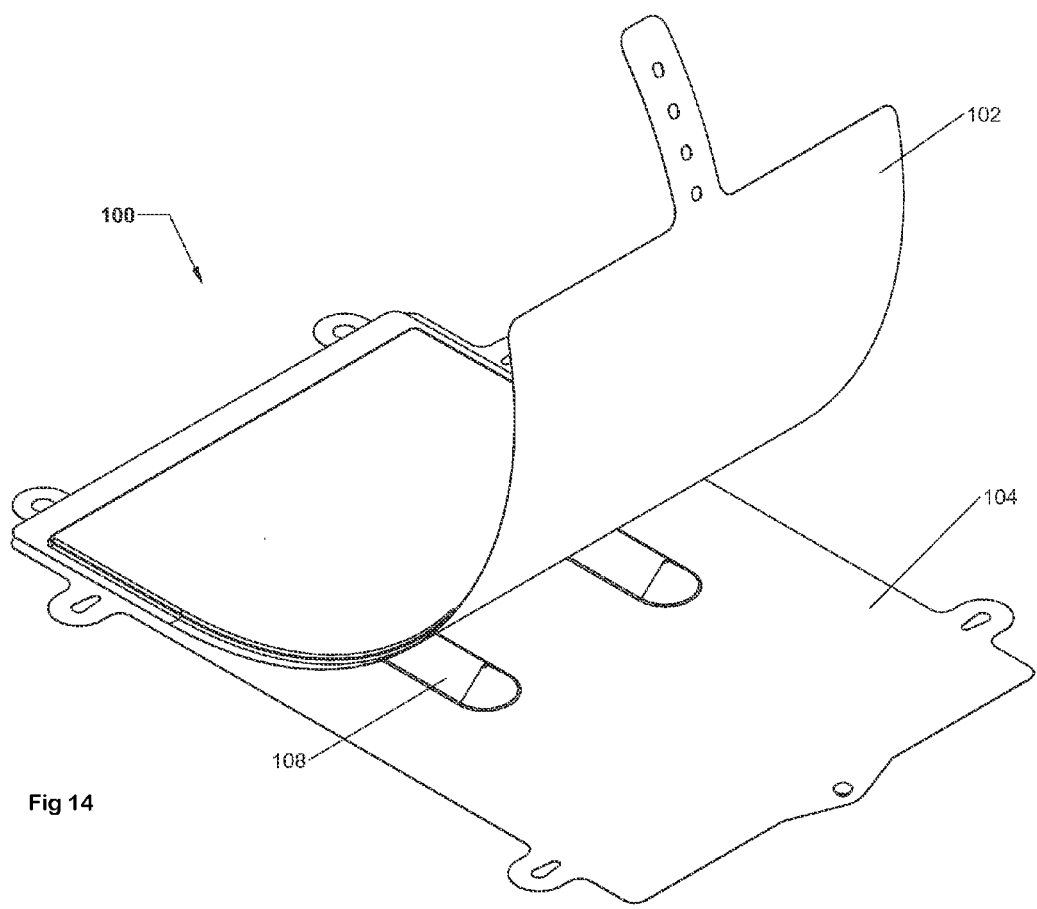
FIG. 14 is a perspective view of a heated pediatric mattress overlay or pad in accordance with embodiments of the invention.
Figure 15:
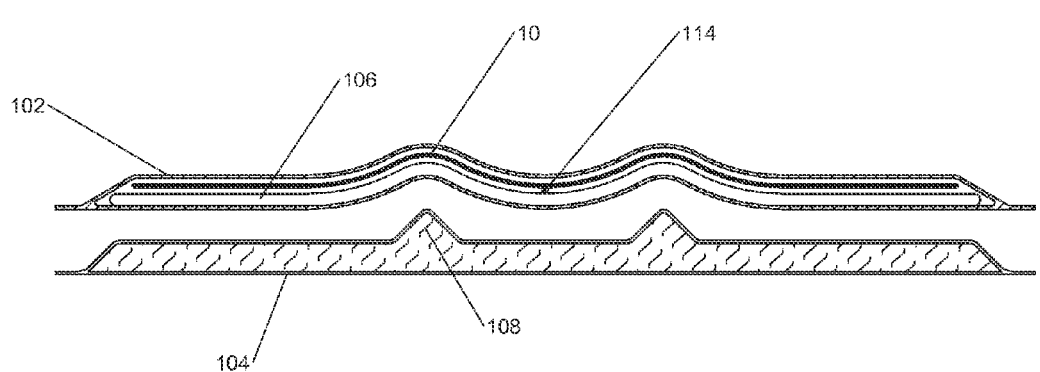
FIG. 15 is a cross sectional view of a heated pediatric mattress overlay or pad in accordance with embodiments of the invention.

Some of the embodiments of the heated underbody warming system with electrosurgical grounding include a base layer 104 that can be attached to the surgical table (FIGS. 14-16). The base layer 104 includes one or more layers of polymeric foam material that can provide a degree of pressure relief as well as a degree of planar stiffness to help maintain the planar shape of the base layer. Preferably, the compressible material layer 20, (e.g., foam 20) material is covered on both sides by two layers of plastic film material (e.g., 40, 42) that are bonded together around their periphery to form a substantially hermetically sealed pouch. The bond may be a thermal bond such as a heat seal, RF weld or ultrasonic weld. Alternately it can be an adhesive or solvent bond or sewn. The foam layer 20 serves as a pressure reduction material and gives the lower layer enough planar stiffness to prevent it from folding or bunching into a wad of plastic film.

Preferably, the conductive or semi-conductive coating of the heater material 10 is a polymer and the bonding process is polymerization. Polymerization results in a very secure bond. The coating on each individual thread allows maximal flexibility and does not crack, fracture or delaminate during flexion. Polymerization of these conductive or semi-conductive materials on individual fibers of the carrier fabric is the optimal process for producing a durable, flexible and stretchable heater. Semi-conductive polymer coatings such as polypyrrole, are preferred for this invention. However, other coating processes are anticipated and conductive coatings that use carbon or metal as the conductive material are also anticipated.

The result is an electrically semi-conductive fabric heater material that is highly flexible, durable, will not fracture either the carrier fiber or the semi-conductive polymer coating with repeated flexing, loading and stretching. Additionally, the heater fabric of this invention does not require lamination between layers of plastic film for protection or stabilization.

Figure 4A:
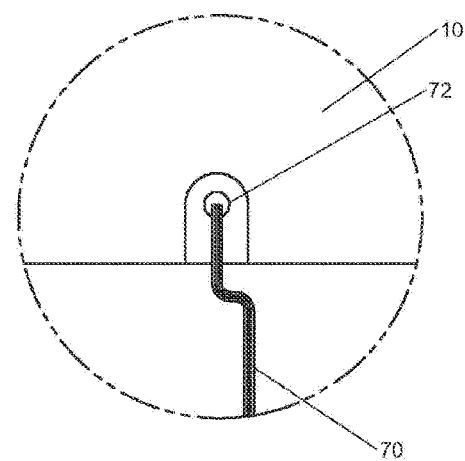
FIGS. 4A and 4B are an illustration the return electrode wire connection to a portion of a heater assembly in accordance with embodiments of the invention.
Figure 4B:
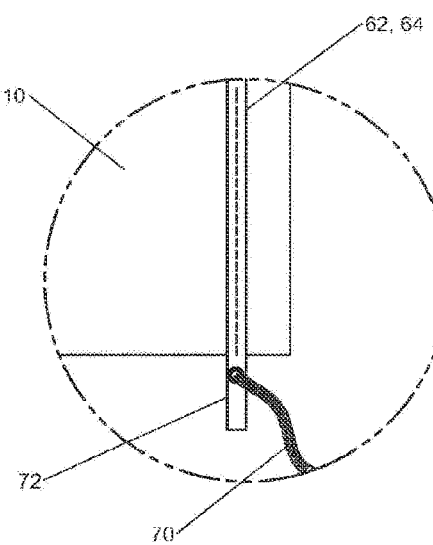

As shown in FIG. 4A, an electrosurgical return electrode wire 70 may be electrically connected 72 directly to the heating element 10. Alternately, as shown in FIG. 4B, an electrosurgical return electrode wire 70 may be electrically connected 72 directly to one of the bus bars 62, 64. The return electrode wire 70 exits the shell 40, 42 of the underbody support and can be connected to the grounding return of an electrosurgical generator.

The fabric heater of this invention may be coated with a thin layer of elastomeric material such as silicone rubber. Other elastomers are also anticipated. The purpose of coating one or both sides of the heater element with an elastomer in this invention is to protect the heater fabric from damage by liquids and oxidation. The coating of silicone rubber also provides electrical insulation in the event that adjacent areas of heater surface contact one another, shorting the electrical pathway or a hole occurs in the shell. Very thin layers of silicone rubber will suffice and add minimal stiffness to the construction. Alternately, thermoplastic elastomers or plastic films can be applied to one or both sides of the heater material.

As shown in FIG. 8, the sheet-like heating element 10 is enclosed between two sheets of shell material 40, 42 that are bonded together around their periphery 48. The heater is thus encased in a substantially hermetically sealed pouch.

The shell 40, 42 protects and isolates the heater assembly from an external environment of the mattress and may further protect a patient disposed on the mattress from electrical shock hazards. According to preferred embodiments of the present invention, the shell is waterproof to prevent fluids, for example, bodily fluids, IV fluids, or cleaning fluids, from contacting the heater assembly, and may further include an anti-microbial element, for example, being a SILVERion™ antimicrobial fabric available from Domestic Fabrics Corporation.

In the preferred embodiment of the shell 40, 42, a layer of plastic film 40, 42 is placed over each broad surface of the heater assembly, but is not bonded to the heater assembly (FIGS. 8 and 10). The two layers of plastic film are bonded to each other around the periphery 48 of the heater assembly to form a water-resistant shell 40, 42. The bond may be from heat, radio frequency (RF), ultrasound, solvent or adhesive. Alternatively, the bond may be a sewn connection or a combination of sewing and adhesive. The preferable bond construction around the periphery of the mattress creates a durable shell without folds, creases, crevasses or sewing needle holes that can collect infectious debris and be difficult to clean. The bonds of this invention are easy to clean.

In some embodiments, a heated mattress for pediatric use 100 may include an upper heated layer 102 that is separate from a lower base layer 104 as shown in FIGS. 14 and 15. The upper heated layer 102 may also include a layer of thermal insulation material 106, preferably located on the underside of the heater element 10, away from the patient contact surface. Preferably the thermal insulation layer 106 is a high-loft fibrous insulation, for example Thinsulite™ (3M, St. Paul, Minn.).

As shown in FIG. 14, the upper heated layer 102 is attached to the lower base layer 104 in a way that maintains the alignment of the upper heated layer 102 as it rests on the lower base layer 104 yet allows maximal independent flexion between the two layers. The preferred attachment location between the two layers is at the foot end periphery of the mattress. Alternately, it could be that the upper heated layer 102 and lower base layer 104 are attached to each other at the head end or in a central region of the heated mattress such as along a longitudinal centerline. These examples are not meant to limit other areas of attachment between the two layers. In a preferred embodiment the heater layer 102 may not be bonded to the base layer 104 across their entire opposing surfaces or around their entire peripheries. The two layers are free to fold and bend substantially independently of one another (FIGS. 14, 16A-D).

Maintaining the alignment of the upper heated layer 102 and the lower base layer 104 helps assure that the heater layer does not slip, perhaps dropping the patient off of the bed. Surgical mattresses are frequently attached to the surgical table and in certain embodiments of this invention, preferably only the base layer 104 is attached (e.g., fixedly coupled) to the table. The attachment between the two layers may be secure enough to assure that the upper heated layer 102 cannot slide independently of the base layer 104.

The attachment between the two layers may be a bond from heat, radio frequency (RF), ultrasound, solvent or adhesive. Alternatively, the attachment may be a sewn or riveted. Finally, the attachment means may be detachable such as buttons, snaps or a Velcro hook and loop connection. Other attachment means are anticipated for this connection between the layers.

By separating the heater layer 102 from the base layer 104, the limitations of the hammocking effect of the foam support can be eliminated. After the patient is positioned substantially in the midline of the mattress, the lateral sides of the heater layer that extend beyond the sides of the patient, can be folded upward so that they closely approximate the sides of the patient (FIGS. 16A-D). This folding of the heater layer's sides upward along the side of the patient is a manual process by the surgical staff. The heater layer 102 is held in the folded position by inserting rolled towels 112 (FIGS. 16B-C) or similar materials such as high-loft fibrous material or polymeric foam between the base layer 104 and the underside of the heated layer 102. Positioning rolled towels at the side of the pediatric surgical patient or even under the patient, is a well-known practice in pediatric patient positioning.

Alternately, the base layer 104 may include two or more elongated longitudinal air bladders 108 near the side edges. The air bladders 108 can be inflated to elevate the sides of the heated layer to a position proximate the side of the patient.

If the attachment between the two layers is not in the longitudinal midline, patient-positioning rolls may be placed under the heated layer 102 to maintain maximal heat transfer characteristics while allowing complex patient positioning. For example, small rolls of towels are frequently placed under the chest/shoulder blades of very small babies in order to put their back into extension and improve access to their upper abdomen. If this positioning roll is placed above the standard heated mattress, the roll lifts half of the patient's body off of the heated surface. Naturally this markedly reduces the heat transfer and capacitive grounding ability of the mattress to the patient. In contrast, this invention allows the positioning roll to be placed under the upper heated layer 102 and the heater thus stays in conductive thermal contact with the entire posterior surface of the patient also maximizing grounding contact.

It has been shown that for optimally safe and effective electric mattress warming, it is believed that the control temperature sensor 114 desirably is touching the patient. Therefore, the control temperature sensor 114 is preferably located near the longitudinal midline of the mattress, where the patient is most likely to lay as shown in FIG. 15. It is easy to assure control temperature sensor 114 contact with an adult patient because they cover most of the surface of the mattress (on a narrow operating table). However, small pediatric patients mal-positioned on the mattress could inadvertently fail to contact the control temperature sensor.

Figure 16A:
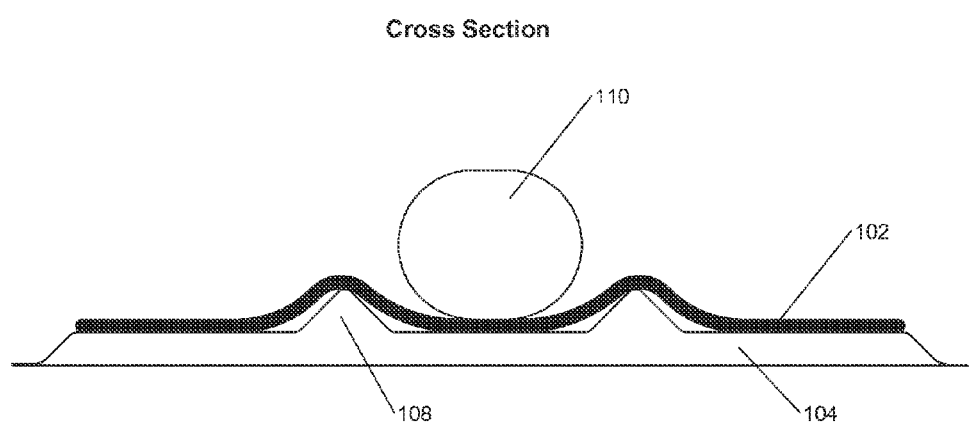
FIGS. 16A-D is a cross sectional view of a heated pediatric mattress overlay or pad in accordance with embodiments of the invention.
Figure 16B:
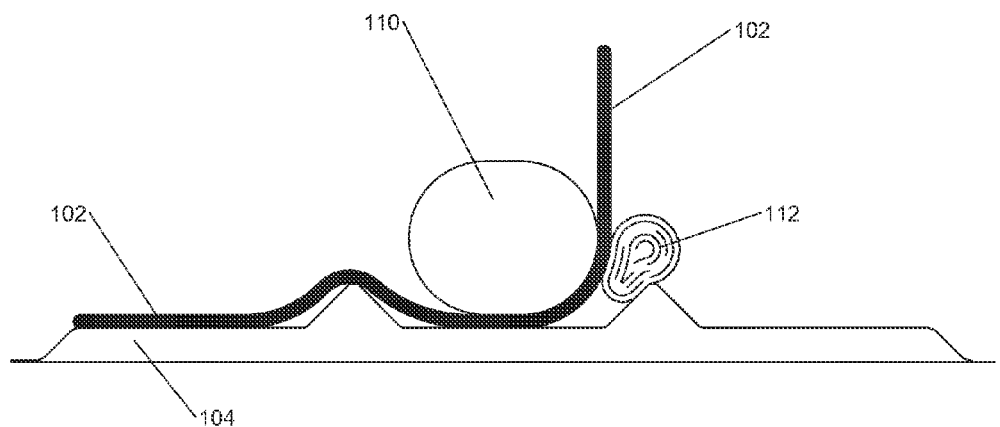

To assure accurate patient positioning relative to the control temperature sensor 114, some embodiments may preferably include two or more substantially elongated positioning members 108 that protrude upward between 0.75 and 2.5 inches from the upper surface of the base layer 104 (FIGS. 14, 15, 16A). The elongated positioning members 108 are preferably made of a compressible foam material. The elongated positioning members 108 are preferably triangular in cross-section, are 4-12 inches long and positioned 5 to 8 inches apart (2.5-4 inches from the midline) in the region of the mattress that corresponds to the location of the patient's torso and legs.

These elongated positioning members 108 may be parallel and project upward into the upper heated layer 102, causing the upper heated layer 102 to form a trough between the positioning members. The midline trough naturally accommodates the baby's body and centers it on the midline (FIGS. 15, 16). If the baby is not centered in the midline of the trough, the foam positioning members 108 will cause the baby to be visibly contorted, alerting the surgical staff that repositioning is required.

As shown in FIG. 15, the control temperature sensor 114 is attached to the heating element 10 in the upper heated layer 102, in a central location that corresponds substantially to the center of the trough. Therefore, the positioning trough created by the elongated positioning members in the base layer, virtually assures that the small baby will be positioned in contact with the control temperature sensor, which is performed for both safety and effectiveness. The control temperature sensor also serves as a safety sensor, detecting excessive heating due to the combined effects of the heater and the capacitive coupling.

Figure 16C:
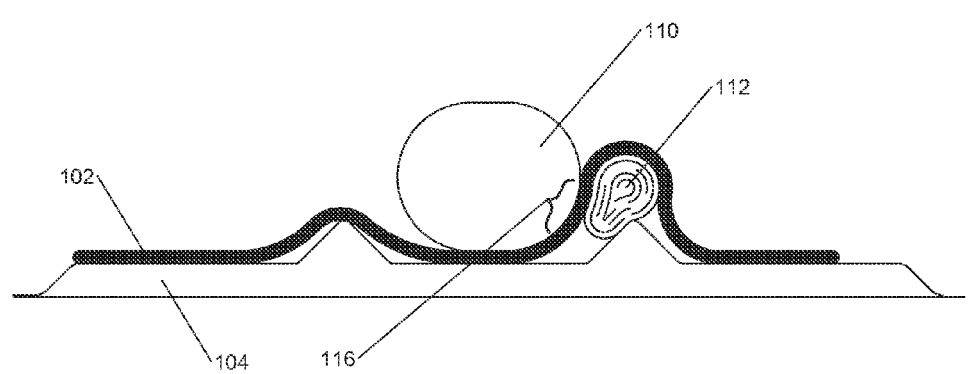
Figure 16D:
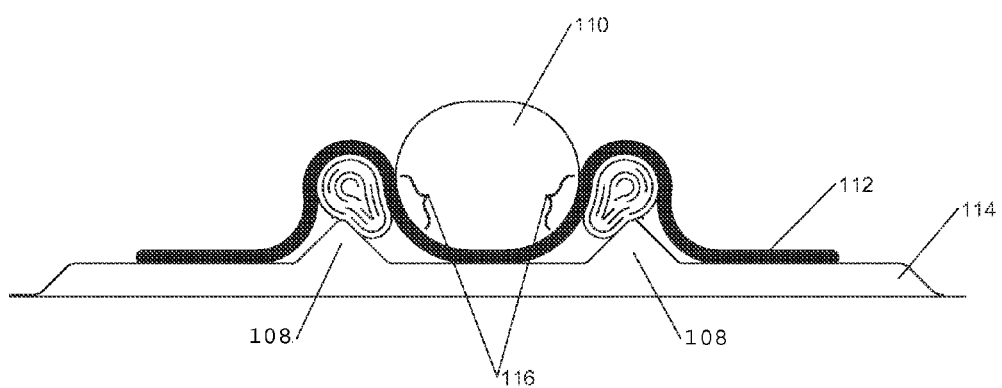

Accordingly, certain embodiments of the invention have a maximally flexible heated layer that is not constrained by laminating it to the layers of polymeric foam that form the traditional heated mattress construction. By substantially separating the heating function 102 from the support function 104, this invention allows the heated layer 102 to maximally contact the non-weight-bearing side surfaces of the patient for added heat transfer 116 (FIGS. 16C, 16D). Especially for the small pediatric patient, the body surface area in contact with the heated surface can approximately double with mattress 100, compared to traditional heated mattresses. The efficiency of capacitive coupling is also dependent on the amount of surface area in contact with the patient. Therefore, certain embodiments of this invention increase the heat transfer effectiveness and capacitive coupling of the mattress, especially in pediatrics, while maintaining safety with regards to patient positioning and folding or bunching of the heater under the patient.

To prevent overheating, certain embodiments include one or more temperature sensor assemblies 114 in the heated underbody support that can sense the temperature in a desired area and then provide feedback to the controller. The temperature sensor assembly 114 can be placed in an area that would be in contact with a patient as described above or in an area that would reflect an average temperature of the heated underbody support. The controller may shut off the power supply to the heating element and/or triggers an alarm, such as an audible or visible alarm, if the sensed temperature is too high, such as if the temperature is at or above a maximum or threshold temperature. Thus, the temperature sensor assembly 114 therefore acts as a safety feature to help protect patients from overheating or being thermally injured.

In some embodiments, the flexible heating element 10 itself may be a temperature sensor. In such embodiments, the flexible heating element 10 is formed of a material having a resistance that varies with temperature. The controller may determine the temperature of the flexible heating element 10 by measuring the resistance or change in resistance in the power supply circuit. The resistance of the heating element 10 may also be used to determine the Watt density output of the heating element 10. Thus, the heating element 10 resistance measurement may be used as a control parameter by the controller to control or adjust the Watt density output of the heated underbody support as desired.

The combination of conductive fabric heating elements 10 made from flexible and stretchable material, bus bars 62, 64 attached near opposing edges 12, 14 of the heating element 10, one or more temperature sensors 114 and a controller, comprises a heater assembly 1 according to some embodiments. The heater assembly 1 may be secured to a compressible material layer 20 such as foam and may be covered with a water-resistant shell 40, 42 that is preferably made of a stretchable plastic film such as urethane or PVC, however, other film materials and fiber-reinforced films are anticipated.

In some embodiments, the underbody support includes a grounding electrode for electrosurgical equipment. As shown in FIGS. 1, 15 the grounding can be accomplished by placing a large electrode (e.g., 10) under the patient, but not in direct electrical contact with the patient. The grounding electrode 10 is preferably substantially the size of that portion of the surgical table mattress (e.g., within a range of standard sizes) under at least the patient's torso. The grounding electrode (e.g., 10) is separated from the patient by one or more layers of electrically insulating material 40 sometimes referred to as a dielectric. This can create a condition of capacitive coupling, for grounding the RF electrical current without actually touching the patient. Capacitive coupling grounding electrodes are well known in the art.

As shown in FIG. 6, in some embodiments the capacitive coupling grounding electrode 10 is the conductive or semi-conductive heating element 10 material which is already in close proximity to the underside of the patient. By using the heating element 10 material as the grounding electrode 10, there is no competition to determine which technology is going to be in the most advantageous position—close to the patient's skin. Both technologies get the same advantageous location. Using a single piece of conductive material, preferably a stretchable conductive or semi-conductive fabric as the heating element 10 and grounding electrode 10, also minimizes the negative effects of multiple layers of materials and laminates being interposed under the patient, which can cause hammocking, thereby reducing the pressure off-loading abilities of the mattress. The fewer the layers of material, the more stretchable and flexible the construction. Avoiding constructions that involve layers of fabric and film to be bonded together forming laminates is performed in order to optimize stretchablity and flexibility.

A semi-conductive polymer such as polypyrrole is advantageous in that it is a preferential RF energy absorber. Polypyrrole can also be polymerized onto fabric and in the process coats each individual fiber, retaining the flexibility and stretchability of that fabric. The polymerization process results in a bond between the fiber and the polymer that is inseparable. This is in contrast to electrically conductive composites made from powdered or vaporized carbon or metals that may be applied to the surface of relatively non-stretching fibers and fabrics such as woven nylon, because such composites will flake off with repeated flexion and stretching. Polypyrrole is, therefore, a preferable conductive material for heaters and grounding electrodes that are to be positioned under a patient because it allows flexion and stretching so that the patient can sink optimally into the support surface below the heater and/or grounding electrode.

Figure 6A:
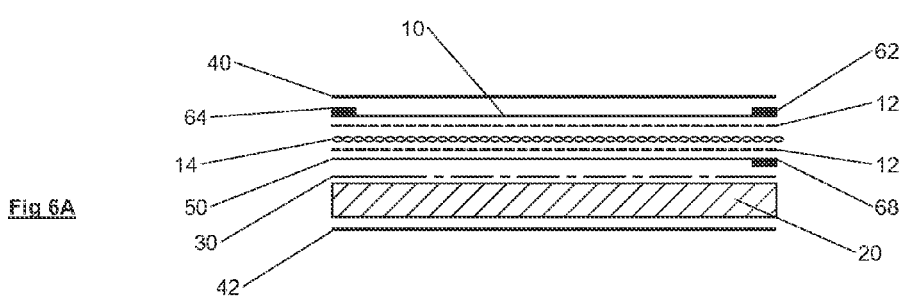

As shown in FIG. 6A, in some embodiments, the grounding electrode 50 is a separate layer of material positioned near and parallel to the heating element 10. In this case, the grounding electrode 50 may advantageously be made of a semi-conductive polymer such as polypyrrole irrespective of what the material the heating element 10 is made. The heating element 10 and grounding electrode 50 may be electrically insulated from each other by applying a coating of elastomeric material 12 such as silicone or rubber to one or both conductors. A layer of electrically insulating material 14 such as fabric, film or foam may be interposed between the heating element 10 and grounding electrode 50. Preferably these layers of electrically insulating materials are not all bonded together into a laminate that would add unnecessary stiffness to the support surface.

Figure 6B:
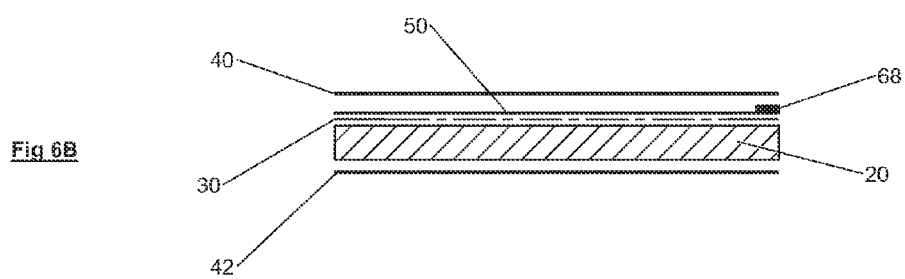

As shown in FIG. 6B, in some embodiments, the grounding electrode 50 is its own layer of material, and there is no heating element. In these cases, the grounding electrode 50 may advantageously be made of a semi-conductive polymer such as polypyrrole because of its flexibility, stretchability, durability, radiolucency and radar-absorbing attributes, compared to other metal coated fabrics.

In some embodiments, the dielectric is the outer shell material 40 of the underbody support. In some embodiments, other layers of material such as fabric or foam 74 (FIG. 7) may be interposed between the shell dielectric material 40 and the heater/grounding electrode material 10. In some embodiments, these layers of materials are preferably not laminated together, thereby maintaining maximal flexibility and stretchablity for accommodating the patient into the mattress.

In some embodiments, one or both sides of the grounding electrode layer 50/10 (or heating element 10) is coated on its upper side with a thin layer of flexible, stretchable elastomeric material such as rubber or silicone. This coating of elastomeric material interposed between the electrode 10 and the dielectric material layers serves as second, redundant, safety dielectric layer should an inadvertent hole be put into the outer shell 40, 42. The redundant dielectric layer would prevent direct electrical coupling between the patient and the grounding electrode material, which could cause a burn.

Preferably, the elastomeric material is applied as a gel or liquid so that it can coat the individual fibers of the grounding electrode layer 50 or heating element 10 before it sets up into its elastomeric solid form. Coating the individual fibers maximally protects the grounding electrode 50 or heating element 10 from moisture damage. It also limits the electrical contact area to an inadvertently cut edge in the exceedingly unlikely event that the both the dielectric and heater layers are cut and the active electrode of the electrosurgical unit is inserted into the cut. In this instance the polymeric heaters fibers at the cut edge would melt and retract from the electrode, automatically limiting the adverse current flow.

In some embodiments, as shown in FIG. 4A, the return electrode wire 70 is electrically connected 72 directly to the grounding electrode (heater) material 10. Since the grounding electrode 10 is the heater material 10, the electrode itself adds resistance to the current flow through the circuit. The further the current may flow through the heater material, the greater the resistance. A return electrode wire 70 connected 72 to one end of the heating element 10 would create a situation wherein the electrical resistance to current flow would be significantly greater for current originating at the far end compared to the end of the patient closest to the wire connection 72.

In some embodiments, as shown in FIG. 4B, the return electrode wire 70 is electrically connected 72 to one of the bus bars 62, 64. Connecting the return electrode wire 70 to the bus bar 62 or 64 is advantageous when the grounding electrode material 10 is a resistive heating element 10 material that adds resistance to the circuit. Since the low resistance bus bar 62, 64 runs substantially parallel to the patient along an edge of the grounding electrode 10, the resistance to the current flow caused by the heating element 10 material is substantially equal along the entire length of the patient that is contacting the grounding electrode 10 creating a safe condition.

In some embodiments, the shared conductive pathway through the heater material 10 involves that the capacitive coupling electrode of the instant invention be adapted to hook to patient warming power supplies and electrosurgical generator that are designed with a "floating" output. By "floating," we mean that the electrical current within each of the respective circuits has no potential or reference with respect to earth (ground) or with respect to the other piece of equipment. This configuration allows simultaneous operation of the patient warming power supply and electrosurgical generator without electrical interference occurring between the two.

In some embodiments, the shared conductive pathway through the heating element 10 material may require that the capacitive coupling electrode of the instant invention be adapted to hook only to patient warming power supplies and electrosurgical units that are designed with a "isolated" output. By "isolated" we mean that the electrical current within each of the respective circuits has no potential or reference with respect to earth (ground). This configuration helps to allow simultaneous operation of the patient warming power supply and electrosurgical unit without electrical interference occurring between the two.

In some embodiments, the shared conductive pathway through the heating element 10 material may require that the capacitive coupling electrode of the instant invention be adapted to hook only to patient warming power supplies that supply a low voltage direct current (48 volts or less) and an electrosurgical unit that supplies an RF current. This configuration helps to allow simultaneous operation of the patient warming power supply and electrosurgical unit without electrical interference occurring between the two.

In FIGS. 1 and 10, the shell 40, 42 protects and isolates the heater assembly 1 from an external environment of the heater assembly 1 or heated underbody support and may further protect a patient disposed on the heated underbody support from electrical shock hazards. According to preferred embodiments, the shell 40, 42 is waterproof to prevent fluids, for example, bodily fluids, IV fluids, or cleaning fluids, from contacting the heater assembly 1, and may further include an anti-microbial element, such as SILVERion® antimicrobial fabric available from Domestic Fabrics Corporation (Kinston, N.C.), which is extruded in the plastic film of the shell material.

As shown in FIGS. 8 and 10, in some embodiments, a layer of plastic film is placed over each broad surface of the heater assembly 1, as an upper shell 40 and a lower shell 42 but is not bonded to the heater assembly. The two layers of plastic film are bonded to each other around the periphery 48 of the heater assembly 1 to form a water-resistant shell 40, 42. The bond may be from heat, radio frequency (RF), ultrasound, solvent or adhesive, for example. The heater assembly 1 may be "free floating" within the shell with no attachment to the shell 40, 42, or can be attached to the shell, such as only at the edges of the heater assembly 1 as described above, for example. This bond construction around the periphery 48 of the heated underbody support creates a durable shell without folds, creases, crevasses or sewing needle holes that can collect infectious debris and be difficult to clean. The heater assembly 1 covered by a shell of plastic film and optionally including a foam or other support layer comprises a heated mattress, mattress overlay, or pad according to some embodiments.

Figure 18:
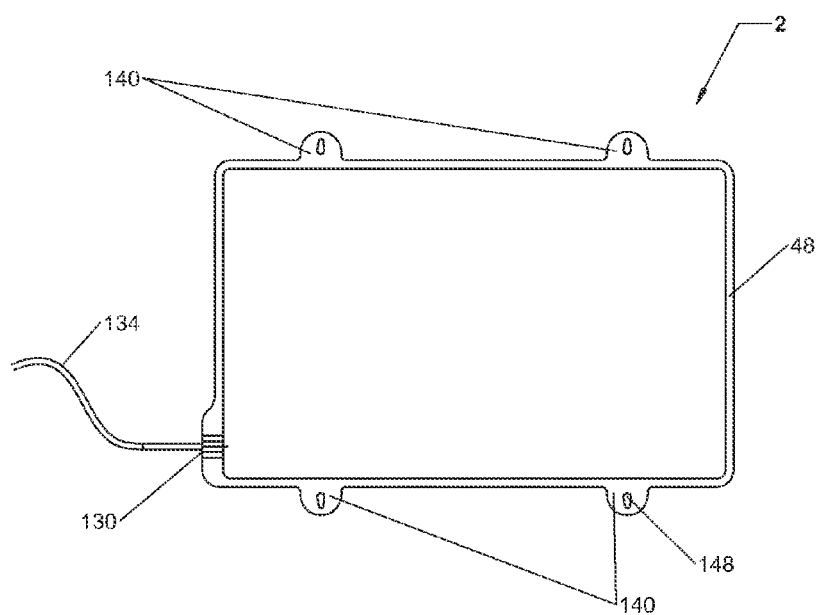
FIG. 18 is an illustration of a heated mattress overlay or pad with attachment tabs in accordance with embodiments of the invention.

In certain embodiments, such as the embodiments shown in FIGS. 17 and 18, the shell 40, 42 construction allows the power entry module 130 to be located and bonded between the shell, such as the layers of plastic film 40, 42, at the edge of the shell within the bonded layers 48 (FIG. 18). The power entry module 130 can be bonded with adhesive, solvent or heat, for example, between the adjacent layers of upper and lower shell 40, 42. Sewn shell constructions known in the art prevent the power entry from being located at the sewn edge and result in the power entry being located on the flat surface of the shell rather than the edge, which may result in the patient laying on the hard lump created by the power entry module and which could contribute to the formation of a pressure injury. In some embodiments, the power entry module 130 is a piece of molded plastic, for example in a shield-shape, that can be sealed between the sheets 42 and 44 in the peripheral bond 48 edge seal of the shells 42, 44. The pointed ends of the shield-shaped power entry module 130 allows the shells 42, 44 to transition smoothly from the area where the upper and lower shells 42, 44 are sealed to each other, to the adjacent area where the shells 42, 44 are sealed to the power entry module 130 and then back to the shells 42, 44 being sealed to each other. In some embodiments, the power entry module 130 includes a tubular channel 132 traversing from the outer side to the inner side of the shell. The tubular channel 132 may be sized to accommodate the wire cable 134 that contains the power and sensor wires. The wire cable 134 can pass through the tubular channel 132 from the outside to the inside of the heated underbody support and can be adhesive, solvent or heat bonded to the power entry module in this position, creating a water-tight seal. In another embodiment, the power entry module 130 may be shaped and sized to house a plug-in connector. In some embodiments, the return electrode wire 70 (e.g., FIGS. 4A, 4B) that connects to the electrosurgical generator can pass through an identical tubular channel 132 from the inside to the outside of the heated underbody support as the power entry module 130, which is used for the power cable 134 to exit the shell.

The heater assembly 1 of these inventions can be encased in a shell of plastic film as described, or may have no shell. With or without a shell or compressible material layer 20, it can be used as a mattress overlay on top of, or can be inserted into, a pressure reducing mattress. For example, since pressure reducing mattresses typically have water resistant covers, the heater assembly 1 may be inserted directly into the mattress, inside the mattress cover, without a shell on the heater assembly 1. In either case, the heated underbody support is designed to have little or no negative impact on the pressure reducing capabilities of the mattress on which it is laying or into which it is inserted.

When used as a mattress overlay, the shell of the heater assembly 1 is preferably water resistant, flexible, and durable enough to withstand the wear and tear of operating room use. Examples of materials which may be used for the shell include urethane and PVC. Many other suitable plastic film or fiber-reinforced plastic film shell materials are anticipated. In some embodiments, the shell material is about 0.010-0.015 inch thick. In this thickness range, both urethane and PVC, for example, are strong but retain an adequate stretchability. The heated underbody support may cover approximately the entire surface of the surgical table or any other bed. Alternately, the heated underbody support may be sized to fit some or all of the cushion that form the support surface of a surgical table. For example, if the cushion has multiple separate sections, such as three, the heated underbody support may be sized to fit over one or two or all three of the cushion sections.

Figure 19:
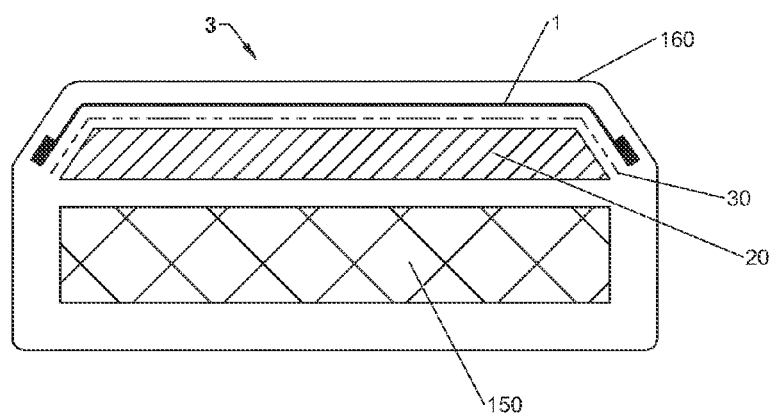
FIG. 19 is a cross sectional view of a heated mattress including a visco-elastic foam layer in accordance with embodiments of the invention.

As shown in FIG. 19, in some embodiments, compressible material layer 20 or foam layer 150 may be high tech foam to reduce the pressure exerted against the patient's skin during surgery. High tech foams include but are not limited to visco-elastic foams that are designed to maximize accommodation of the patient into the mattress. As previously noted, accommodation refers to the sinking of the user, such as the patient, into the underbody support until a maximal amount of support surface area is in contact with a maximal amount of skin surface, and the pressure exerted across the skin surface is as uniform as possible. These high tech foam materials may accommodate the patient more effectively than simple urethane upholstery foam. Unlike other mattress heaters or heating materials, the unique stretchable, flexible, free floating design of the heater assemblies 1 described herein allow them to overlay a layer of visco-elastic foam and maintain the accommodation properties of the foam. Further, the heater assembly 1 of this invention is soft, flexible and stretchable enough to be the separated from the patient by only a single layer of plastic film and still be comfortable. The avoidance of multiple layers of materials interposed between the patient and the mattress foam maximizes accommodation and heat transfer.

In embodiments, such as depicted in FIG. 19, a heated mattress 3 including one or more foam layers 150, a water-resistant shell or cover 160 may encase the foam 150. The foam 150 may be simple urethane foam or high-tech foam such as visco-elastic foam, for example. The cover 160 may be made of plastic film that has been extruded onto a woven fabric (e.g., Naugahyde®). In one embodiment, the heater assembly 1 may be located within or may be removably inserted directly into the mattress cover 160, with or without a shell 40 on the heater assembly 1. The heater assembly 1 may be placed directly on top of the mattress foam 150 inside the cover 160 or a heater assembly 1 (with its own shell) may be placed on top of a mattress outside of the mattress cover 160. If a foam mattress has its own shell, the thickness of the shell 40 of the heater assembly 1 can be reduced to, for example, about 0.003-0.010 inch, or omitted, because the heater assembly 1 is protected from mechanical damage by the cover 160 of the mattress 150. The thinner shell material improves the stretch-ability of the shell. Alternately, the heating element 10 may be bonded directly to the mattress foam 150.

The thermal effectiveness of this heated underbody support 3 can be optimized when the heating element 10 is overlaying a layer that can provide maximal accommodation of the patient positioned on the support. In this condition, the heating element 10 is in contact with a maximal amount of the patient's skin surface which maximizes heat transfer. Heated underbody supports made with inflatable air chambers have been shown to provide excellent accommodation. Further, a heated underbody support with excellent accommodation properties having a heating element 10 of this design avoids degrading the accommodation properties of the mattress when a heater assembly 1 is added. Therefore, the combination of the heater assembly 1 design of the instant invention, with an accommodating mattress such as a mattress made with inflatable air chambers 170 as shown in FIG. 20, is uniquely advantageous and synergistic for the effectiveness of both technologies.

Figure 20:
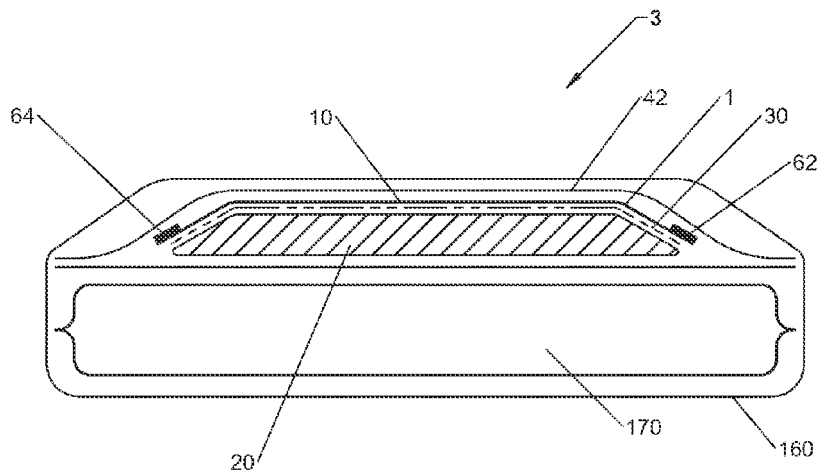
FIG. 20 is a cross sectional view of a heated mattress including an inflatable chamber in accordance with embodiments of the invention.

An embodiment of a heated mattress 3 comprising one or more air chambers 170, 172 and a heater assembly 1 overlaying the one or more air chambers 170, 172 is shown in FIGS. 20, 21 and 22. In some embodiments, a single air chamber 170 or a plurality of elongated inflatable chambers 172 are positioned under the heater assembly 1. The plurality of elongated inflatable chambers 172 may be oriented in parallel and positioned side-by-side one another, with their long axes extending substantially from one side of the mattress to the other side. However, other inflatable chamber shapes and orientations are anticipated. The inflatable chambers 172 may be round or ovoid in cross section. They may or may not be physically secured to the adjacent air chamber. Alternately, they could be secured to a base sheet or simply positioned and contained within the mattress cover 160. The chambers 170, 172 may be made of a fiber-reinforced plastic film or a plastic film that has been bonded, laminated or extruded onto a woven or non-woven fabric reinforcing layer. Urethane may be used as the plastic film, but other plastic film materials are anticipated. Woven nylon may be used as the reinforcing layer, but other fabric materials are anticipated.

The inflatable chamber 170 or chambers 172 can be sealed and static, or connected together in fluid connection to allow redistribution of air between the chambers 172. In some embodiments, the chamber 170 or chambers 172 can be actively inflated and deflated while the heated mattress 3 is in use. The inflatable chambers 172 may be inflated and deflated independently, simultaneously or in groups, while the heated mattress 3 is in use. In some embodiments, the chambers 172 are each a part of two separate groups and are segregated by every other chamber according to their relative positions. A conduit or conduits may be in independent fluid communication with each chamber 172 of the group of inflatable chambers for independently introducing or removing air from that group of inflatable chambers.

Alternately, there may only be a single group of chambers 172 or there may be more than two groups of chambers 172 which can be separately inflated or deflated. If multiple groups of chambers 172 are used, they may not be evenly or symmetrically arranged. For example, chamber groups may alternate under the weight-bearing areas such as the torso and hips. Chambers 172 in areas bearing less weight, such as those supporting the head and legs, may be a single group of chambers 172. In this way, the lighter portions of the patient's body may be supported by chambers 172 that are inflated to a lower air pressure than chambers 172 that support more weight/heavier body portions.

If the chambers 172 are secured to the adjacent chamber or to a base sheet or are secured by the ends to an element running along each side of the mattress 3, it is preferable that the chambers 172 and their means of fluid connection be individually detachable. In this instance, if a single chamber 172 or means of fluid connection fails or is damaged, it can be replaced without requiring the replacement of the entire inflatable heated mattress 3.

The material forming the chamber 170 or chambers 172, such as a plastic film, may be bondable with RF, ultrasound, heat, solvent, or other bonding techniques. The film or film layer of the laminate may be folded back on itself and a single longitudinal and two end bonds may cooperate to form an inflatable chamber 170, 172. More complex chamber construction and bonding embodiments are anticipated.

The conduit fluid connection between the inflatable chambers 172 may be plastic tubing, for example. The inlet into the inflatable chamber 172 can be through one of the bonded seams or may be through a surface of the chamber 172. To prevent occlusion of the tubing at the inlet, the tubing may advantageously extend one or more inches into the chamber. Other conduits are anticipated, such as a molded or inflatable plenum that may run the length of the heated mattress 3.

In some embodiments, a heater assembly 1 (such as a heater assembly 1 encased within a water resistant shell) is placed on top of the inflatable chambers 170, 172 so that the conductive fabric heating element 10 is near the top surface of the heated mattress 3. Alternately, a heater assembly 1 (without a shell) could be placed on top of the inflatable chambers 170, 172 so that the heating element 10 is near the top surface of the mattress. The heated mattress 3 may include a flexible, water resistant cover that encases the heater assembly 1 and the inflatable chambers 170, 172.

In some embodiments, the water resistant mattress cover 160 is a plastic film laminated or extruded onto a woven or knit fabric such as "Naugahyde®". This construction is well-known to be soft and durable and has been used extensively for covering surgical table mattress and other therapeutic mattress. Alternately, the cover 160 can be made of plastic film, fiber-reinforced plastic film or a plastic film laminated or bonded to a woven, non-woven, or knit fabric.

The heater assembly 1 of the heated mattress 3 may be "free floating" within the water resistant cover 160 of the heated mattress 3. Alternately, the heater assembly 1 may be attached to the chamber 170 or chambers 172 or foam 150 or attached to the cover 160, either at the edges of the heater assembly 1 or on or across the top or bottom surface of the heating element 10.

The inflatable heated mattress 3 may include one or more pressure sensor assemblies capable of detecting in real time the actual internal air pressure of the inflatable chambers 170, 172 and may also include a control assembly comprising a comparator for comparing a desired internal air pressure value of the inflatable chambers 170, 172 with the actual internal air pressure and a pressure adjusting assembly for adjusting the actual internal pressure. The control assembly may be activated by active feedback data derived from the comparator for maintaining a desired internal pressure value in the inflatable chambers 170, 172 by adjusting the inflation of the air chamber 170 or of the first and second groups (or multiple groups) of inflatable chambers 172.

Figure 23:
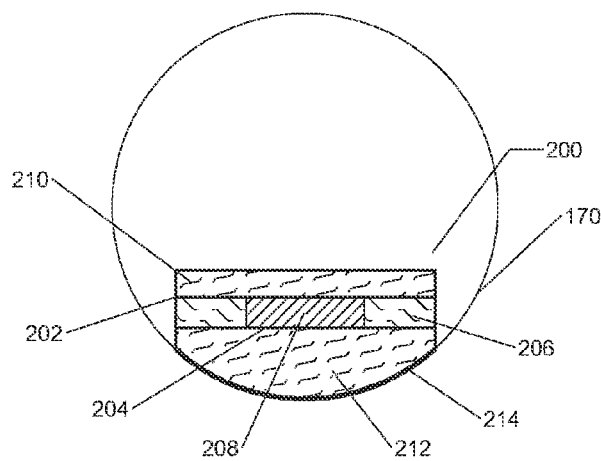
FIG. 23 is a cross sectional view of an inflatable chamber in accordance with embodiments of the invention.
Figure 24:
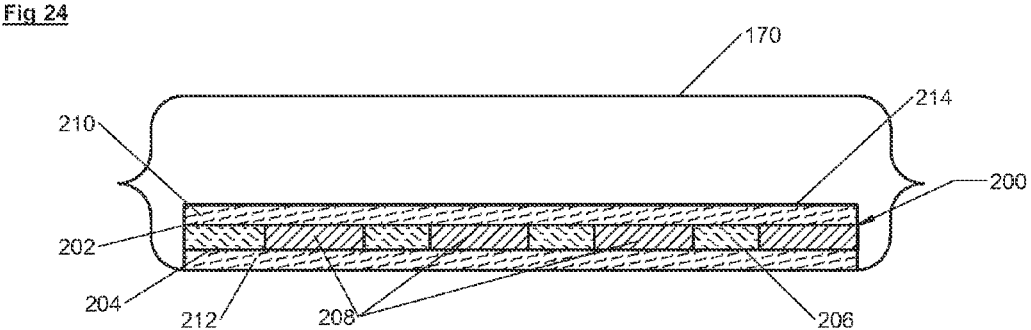
FIG. 24 is a cross sectional view of an inflatable chamber in accordance with embodiments of the invention.

As shown in FIGS. 23 and 24, in some embodiments, in addition to, or in place of pressure sensors, the underbody support (e.g., 3) includes flexible, preferably radiolucent compression sensing switches 200 within one or more of the inflatable chambers 170. These switches 200 are sized to detect when the patient has sunk into a partially inflated mattress 3 to a point of "maximal accommodation." The switches 200 have a large surface area preferably extending substantially the entire length of the inflatable chamber 170. These compression sensitive switches 200 are positioned to detect the body part that is protruding down into the support mattress 3 the furthest and to prevent that body part from "bottoming out" or touching the hard surface below the underbody support. The height of the inflatable chamber(s) at this point is determined by the volume of the air in the chamber, not the pressure of the air in the chamber.

In some embodiments, the controller algorithm of the inflatable underbody support 3 initiates the release of air from the inflated chambers 170 after the patient is positioned on the support 3. The release of air allows the patient to sink into the support for maximal surface contact and therefore minimal surface contact pressure. Maximal surface contact occurs just before the most protruding body part "bottoms out" on the hard surface below. To achieve this, the air may be released from the chambers 170 and the patient may be allowed to sink into the support until the most protruding body part reaches a predetermined distance from the bottom. At that point the most protruding body part contacts and closes one or more of the flexible, radiolucent compression sensing switches 200. The closed switch allows a small electric current to flow to the controller which responds by stopping the air release and initiates the next sequence in the controller algorithm. In some embodiments, the controller algorithm then energizes the air pumps to re-inflate the inflatable chambers until the most protruding body part no longer compresses the compression sensing switch(es) and the electric current no longer flows through the switch. In this position, the most protruding body part is accurately positioned at a predetermined distance above the hard base surface. With the compression sensing switch(es) in the open position, it can then function as a safety sensor, detecting shifts in patient positioning or loss of air from the inflatable chambers that may result in inadvertent "bottoming out." Should the compression sensing switch(es) close at this point, the controller algorithm may automatically add more air to the inflatable chambers 170 until the switch(es) opens and/or may activate an alarm.

Figure 25:
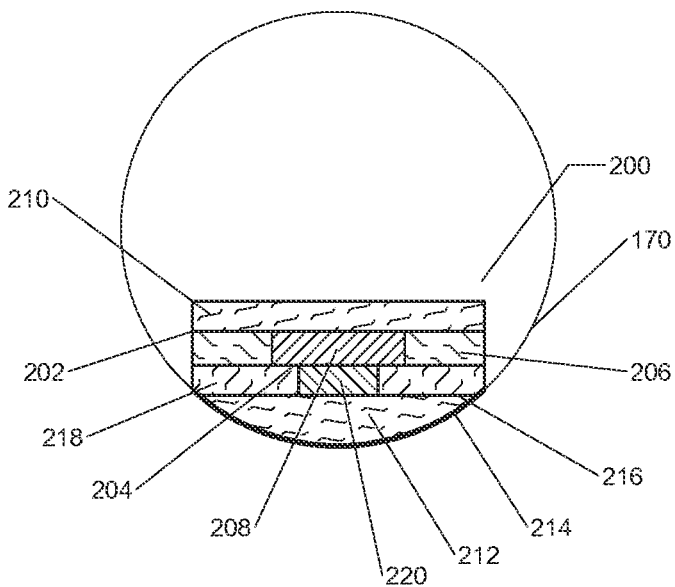
FIG. 25 is a cross sectional view of an inflatable chamber in accordance with embodiments of the invention.

As shown in FIG. 25, in some embodiments, there may be two layers of compression sensing switches 200 stacked on top on each other. The first layer switch 202/204 may be made of a compressible first switch layer 206 comprising softer foam materials or larger holes 208 that allow the switch to close with a certain amount of compression. The second layer switch 204/216 may be made of a compressible second switch layer 218 comprising firmer foam materials or have smaller holes 220 that require more compression in order to close the switch. In this configuration, the air may be released from the inflatable chambers until the patient sinks to a level that closes a first layer switch 202/204. Closing the first layer switch 202/204 stops the release of air. With the second layer switch 204/216 still in the open configuration, the controller "knows" precisely where the most protruding part of the patient is located relative to the top of the table. If the second layer switch 204/216 were to subsequently close, the controller would "know" that either the patient had shifted positions or additional air had leaked from the system allowing the most protruding part to be too close to the hard surface below, triggering air pumps to re-inflate the chamber 170 until the second layer switch 204/216 opens. Maintaining the air volume in the inflatable chambers 170 at a level that causes the patient to close the first layer switch 202/204 while leaving the second layer switch 204/216 in the open position assures very precise positioning of the patient relative to the hard surface below. In this condition, the open second layer switch 216 serves as a safety monitor for unexpected deflation. These compression-sensing switches 200 accurately and precisely control the volume of air within the inflatable chamber 170, not the pressure of the air within the inflatable chamber 170.

The controller may be operationally connected to a first conduit and a second (or multiple) conduit and a pump for inflating the air chamber 170 or plurality of inflatable chambers 172. Each chamber 172 of the plurality of chambers 172 may be independently mounted of each other chamber 172 so that each chamber 172 may react to air pressure changes independently or in concert with the air pressure changes in the other chambers 172. The air may be redistributed within the chambers 172 and the interface pressure may be maintained at any point on the top surface of each of the plurality of chambers 172 which is engaged with an anatomical portion of the user's body, at an average pressure below a capillary occlusion pressure threshold of 32 mm Hg, for example.

In the foregoing detailed description, the embodiments of the invention have been described with reference to specific embodiments. However, it may be appreciated that various modifications and changes can be made without departing from the scope of the embodiments of the invention as set forth in the appended numbered embodiments.

What is claimed is:

1. A heated underbody support with electrosurgical grounding comprising a heated mattress, heated mattress overlay, or heated pad for supporting a person, the heated underbody support with electrosurgical grounding comprising:
   a flexible heating element comprising a sheet of conductive or semi-conductive material having a top surface, a bottom surface, a first edge and an opposing second edge, a length along the first and second edges, and a width extending from the first edge to the second edge;
   a first bus bar extending along the entire first edge of the heating element, the first bus bar adapted to receive a supply of electrical power;
   a second bus bar extending along the entire second edge of the heating element;
   a temperature sensor;
   a layer of compressible material having a top surface and a bottom surface adapted to conform to the person under pressure from the person resting upon the support, and to return to an original shape when the pressure is removed, the layer of compressible material located beneath the heating element;
   a water resistant shell encasing the heating element, the first and second bus bars, and the temperature sensor; and
   a return electrode wire electrically connected to the flexible heating element and adapted to connect to an electrosurgical generator.

2. The heated underbody support with electrosurgical grounding of claim 1, wherein the water resistant shell comprises an upper shell and a lower shell that are sealed together along their edges to form a bonded edge.

3. The heated underbody support with electrosurgical grounding of claim 1, wherein the shell forms a dielectric layer between the heating element and the patient.

4. The heated underbody support with electrosurgical grounding of claim 1, wherein the semi-conductive material comprises fabric coated with polypyrrole.

5. The heated underbody support with electrosurgical grounding of claim 1, wherein the conductive material comprises film coated with conductive ink or impregnated with carbon or other conductive metals.

6. The heated underbody support with electrosurgical grounding of claim 1, wherein the conductive material comprises carbon fiber fabric.

7. The heated underbody support with electrosurgical grounding of claim 1, wherein the compressible material comprises a foam material.

8. The heated underbody support with electrosurgical grounding of claim 1, wherein the compressible material comprises one or more flexible air filled chambers.

9. The heated underbody support with electrosurgical grounding of claim 1, wherein the temperature sensor is adapted to detect the temperature resulting from the heat produced by the heating element plus the heat produced by the capacitive coupling of the heating element when the return electrode wire is attached to an electrosurgical generator that is in use.

10. The heated underbody support with electrosurgical grounding of claim 1, wherein the return electrode wire is electrically connected to either the first or second bus bar.

11. The heated underbody support with electrosurgical grounding of claim 1, wherein the return electrode wire is electrically connected to either bus bar and the bus bar is substantially the same distance from the area of the heating element contacting the patient, along its length, producing a substantially uniform resistance to the electrical current flowing through the heating element to the bus bar attached to the return electrode wire.

12. The heated underbody support with electrosurgical grounding of claim 1, wherein the heating element is the grounding electrode.

13. The heated underbody support with electrosurgical grounding of claim 1, wherein the heating element is the grounding electrode and is stretchable in at least one dimension.

14. The heated underbody support with electrosurgical grounding of claim 1, wherein one or both surfaces of the heating element are coated with an elastomeric coating that serves as a second, safety dielectric layer between the heating element and the patient.

15. The heated underbody support with electrosurgical grounding of claim 14, wherein the elastomeric coating comprises a rubber or silicone material.

16. A heated underbody support with electrosurgical grounding comprising a mattress, mattress overlay, or pad for supporting a person, the underbody support with electrosurgical grounding comprising:
   a flexible grounding electrode comprising a sheet of semi-conductive material having a top surface, a bottom surface, a first edge and an opposing second edge, a length, and a width;
   a return electrode wire electrically connected to the flexible grounding electrode and adapted to connect to an electrosurgical generator;
   a first bus bar extending along the entire first edge of the flexible grounding electrode, the first bus bar adapted to receive a supply of electrical power;
   a second bus bar extending along the entire second edge of the flexible grounding electrode;
   a temperature sensor;
   a layer of compressible material having a top surface and an opposing bottom surface adapted to conform to the person under pressure from the person resting upon the support, and to return to an original shape when the pressure is removed, the layer of compressible material located beneath the flexible grounding electrode; and
   a water resistant shell encasing the flexible grounding electrode.

17. The heated underbody support with electrosurgical grounding of claim 16, wherein the water resistant shell comprises an upper shell and a lower shell that are sealed together along their edges to form a bonded edge.

18. The heated underbody support with electrosurgical grounding of claim 16, wherein the semi-conductive material comprises fabric coated with polypyrrole.

19. The heated underbody support with electrosurgical grounding of claim 16, wherein the conductive material comprises film coated with conductive ink or impregnated with carbon or other conductive metals.

20. The heated underbody support with electrosurgical grounding of claim 16, wherein the conductive material comprises carbon fiber fabric.

21. The heated underbody support with electrosurgical grounding of claim 16, wherein the compressible material comprises a foam material.

22. The heated underbody support with electrosurgical grounding of claim 16, wherein the compressible material comprises one or more flexible air filled chambers.

23. The heated underbody support with electrosurgical grounding of claim 16, wherein the return electrode wire is electrically connected to either bus bar and the bus bar is substantially the same distance from the area of the heating element contacting the patient, along its length, producing a substantially uniform resistance to the electrical current flowing through the heating element to the bus bar attached to the return electrode wire.

24. The heated underbody support with electrosurgical grounding of claim 16, wherein the heating element is the grounding electrode.

25. The underbody support with electrosurgical grounding of claim 16, wherein one or both surfaces of the grounding electrode are coated with an elastomeric coating that serves as a second, safety dielectric layer between the flexible grounding element and the patient.

26. The heated underbody support with electrosurgical grounding of claim 25, wherein the elastomeric coating comprises a rubber or silicone material.

* * * * *